(12) United States Patent
Sutko et al.

(10) Patent No.: US 8,031,926 B2
(45) Date of Patent: Oct. 4, 2011

(54) DISCRETE EVENT DISTRIBUTION SAMPLING APPARATUS AND METHODS

(75) Inventors: John L. Sutko, Reno, NV (US); Nelson George Publicover, Reno, NV (US); Joshua David Larkin, Reno, NV (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 980 days.

(21) Appl. No.: 11/986,371

(22) Filed: Nov. 21, 2007

(65) Prior Publication Data

US 2009/0116707 A1   May 7, 2009

Related U.S. Application Data

(63) Continuation-in-part of application No. 11/597,028, filed as application No. PCT/US2005/017948 on May 20, 2005, now Pat. No. 7,960,702.

(60) Provisional application No. 60/573,459, filed on May 20, 2004.

(51) Int. Cl.
*G06K 9/00*   (2006.01)
(52) U.S. Cl. ..................... 382/128; 250/395
(58) Field of Classification Search .............. None
See application file for complete search history.

(56) References Cited

U.S. PATENT DOCUMENTS

| | | | |
|---|---|---|---|
| 5,825,033 A | 10/1998 | Barrett et al. | |
| 5,865,978 A | 2/1999 | Cohen | |
| 5,953,133 A | 9/1999 | Fujimiya et al. | |
| 6,271,916 B1 | 8/2001 | Marxer et al. | |
| 6,606,153 B2 | 8/2003 | Marxer et al. | |
| 7,009,172 B2 | 3/2006 | Publicover et al. | |
| 7,115,875 B1* | 10/2006 | Worstell ................. | 250/363.03 |
| 7,670,731 B2* | 3/2010 | Finders et al. ............... | 430/30 |
| 2001/0030800 A1 | 10/2001 | Engelhardt et al. | |
| 2001/0047682 A1 | 12/2001 | Samsavar et al. | |
| 2003/0089162 A1 | 5/2003 | Samsavar et al. | |
| 2007/0097143 A1* | 5/2007 | Ii et al. ........................ | 345/592 |

OTHER PUBLICATIONS

Porta, D., International Search Report for international application No. PCT/US05/017948, 2 pp. (Jul. 11, 2008).
Porta, D., Written Opinion of the International Searching Authority for international application No. PCT/US05/017948, 7 pp. (Jul. 11, 2008).

* cited by examiner

*Primary Examiner* — Tom Y Lu
(74) *Attorney, Agent, or Firm* — Karri Kuenzli Bradley; Klarquist Sparkman, LLP

(57) ABSTRACT

Locations of the origins of "discrete events," e.g., photons or other units of radiant energy are acquired from a specimen with reference to a scan frame or other region of interest of the specimen. The location of origin of a discrete event can be determined from the corresponding location datum as derived from a scan-drive signal, a positional feed-back signal, or by a point in time during a unit of sampling time ("image-acquisition period") at which the event is detected. A probability-density function (PDF) is associated with the detected locations. Summing or other processing of the PDFs is performed to produce imagable data. From the data, images can be produced that require fewer discrete events to converge to an ideal density distribution associated with an image feature than required by pixel-based binning methods. Stored data can be mapped into pixels or voxels of a display or otherwise processed, including post hoc processing.

25 Claims, 8 Drawing Sheets

DISCRETE EVENT DISTRIBUTION SAMPLING APPARATUS AND METHODS

CROSS REFERENCE TO RELATED APPLICATIONS

This application is a continuation-in-part of, and claims priority to and the benefit of, U.S. patent application Ser. No. 11/597,028, filed on Nov. 17, 2006 now U.S. Pat. No. 7,960,702, which is a §371 National Phase of International Application No. PCT US2005/017,948, designating the U.S. and filed on May 20, 2005, which claims priority to and the benefit of U.S. Provisional Application No. 60/573,459, filed on May 20, 2004. The '028 and '459 applications are incorporated herein by reference in their respective entireties.

STATEMENT OF GOVERNMENT SUPPORT

The invention was made by an agency of the United States Government or under a contract with an agency of the United States Government. The name of the U.S. Government agency and the Government contract number are: National Science Foundation, Grant/Contract No. EPS0132556. The U.S. Government has certain rights in the invention.

FIELD

This invention concerns, inter alia, high-sensitivity imaging systems, especially optical systems for sensing radiation, including but not limited to reflected radiation, radiation produced by fluorescence, radiation produced by chemiluminescence, and transmitted radiation. The radiation can be in the form of photons or particles (e.g., electrons). Photons are not limited to visible-light photons.

BACKGROUND

Detecting photons and producing images from a scanned field of view have been performed to produce electronic outputs representing the field of view of an instrument, such as a laser-scanning confocal microscope (LSCM). In this regard, the term "photon" means a unit of electromagnetic energy irrespective of its position in the spectrum, e.g., visible or invisible radiation. In quantum physics, a photon is characterized as an entity having particle and wave characteristics. Other forms of radiation, such as electrons, may also exhibit both particle and wave characteristics. The nature of the present invention and the manner of its use are not dependent on whether the radiant events are photons or other types of elementary particles.

In one prior-art optical-detection technique, photons are directed by a confocal imager in a confocal microscope to be sensed by a detector. A confocal imager comprises a point-source of light that illuminates a spot on or in a specimen. In order to illuminate an entire specimen with the spot, the light source is scanned across the specimen by a beam-steering device using scanners that are well known in the art. An illuminated spot is imaged onto a detector through a pinhole. Detectors comprise, for example, avalanche photodiode arrays or photomultiplier tubes or arrays of such devices.

The light source, the illuminated spot, and the detector have the same foci and are placed in conjugate focal-planes. Hence, they are "confocal" to each other.

The diameter of the pinhole is preferably matched to the illuminated spot through the optics situated between them. Because a small spot is illuminated and detected through a small aperture, light imaged onto the detector comes predominantly from the plane in focus within or on the specimen. The detector produces output pulses indicative of the detected photons.

The output pulses from the detector are processed to provide information such as time-correlated photon-counting histograms and image-generation in conventional laser scanning. In conventional imaging systems, however, photons obtained over each of a number of successive, selected equal time periods defined by a pixel clock are used to generate a respective intensity value assigned to each pixel (a pixel is a two-dimensional area of a portion of an image). Photon counts are "binned," that is, accumulated as groups, during each sampling period; each group corresponds to a pixel location of an image display. (It is noted that the term "binning" is sometimes used to denote lumping pixels together, e.g., as during use of a CCD camera. This is a different use of "binning" than the use of the term herein.) In this manner, a computer builds up an entire image one pixel at a time to produce a two-dimensional image often made up of multiple thousands or millions of pixels. For three-dimensional imaging, successive two-dimensional layers of a specimen are scanned, and the computer builds up an image comprising voxels (three-dimensional pixels).

In producing a conventional image, a scan rate is selected. As scan rate increases, fewer photons per pixel per scan are accumulated, and the intensity of the pixels and their signal-to-noise ratios therefore decrease. As a result, prior-art pixel-based imaging systems face constraints in scan rate with regard to the quality of output signal to be produced. Physical and mechanical constraints, such as the rate at which a scanner can move, are also present. In addition, the number of photon counts in a specimen affects other parameters of image quality relating to intensity. These parameters include signal-to-noise ratio.

As a result, pixel-based scanning typically allows for reduced flexibility in experiment design. Resolution of the location of each photon is limited to the dimensions of a pixel or voxel as applicable. The amount of excitation illumination required for the output data to reach convergence of features of sensed images is proportional to the number of photons that must be produced to provide data sufficient to reach this convergence. When pixels are of smaller dimension and therefore provide fewer photons per scan, specimens would have to be subjected to excitation radiation a larger number of times or the same number of times (but for longer time intervals) than if the pixels were larger.

The requirement for greater illumination has functional drawbacks. In example applications involving fluorescent specimens, many fluorescent molecules under test can fluoresce only a limited number of times. At some point, response to excitation radiation ceases, and an effect known as photobleaching occurs. Over-illumination also presents another drawback. With measurements made in vivo, emission of photons from tissue produces free radicals, which can damage cells. Therefore, over-illumination of tissue can result in photo-toxicity.

A limitation of typical prior-art techniques is that they are optically based. Optically based techniques have an inherent limit of resolution known as a diffraction limit, which may be ~0.6λ, where λ is the wavelength of the illuminating light. The resolving power of a lens is ultimately limited by diffraction effects. The lens's aperture is a "hole" that is analogous to a two-dimensional version of the single-slit experiment. Light passing through the lens interferes with itself, creating a ring-shaped diffraction pattern known as the Airy pattern, that blurs the image. An empirical diffraction limit is given by the Rayleigh criterion:

$$\sin\theta = 1.22\frac{\lambda}{D},$$

where $\theta$ is the angular resolution, $\lambda$ is the wavelength of light, and D is the diameter of the lens. A wave does not have to pass through an aperture to diffract. For example, a beam of light of a finite size passing through a lens also undergoes diffraction and spreads in diameter. This effect limits the minimum size d of spot of light formed at the focal point of a lens, known as the diffraction limit:

$$d = 2.44\lambda\frac{f}{a},$$

where $\lambda$ is the wavelength of the light, f is the focal length of the lens, and a is the diameter of the beam of light, or (if the beam is filling the lens) the diameter of the lens. Techniques that utilize so-called far-field or propagating-wave optics do not afford the opportunity to obtain resolution beyond the diffraction limit.

SUMMARY

The Applicants have discovered, inter alia, methods for retaining data, concerning the locations of discrete events associated with a specimen. Such data are conventionally lost in prior-art pixel-based imaging techniques. For example, conventional methods involving "binning" of photons typically result in loss of data. Also, in conventional pixel- or voxel-based sampling systems, more photons are usually detected than otherwise would be necessary if the system did not lose data from use of the pixel-sampling paradigm. In a conventional pixel-based sampling paradigm, photons collected during a predefined pixel clock interval are summed. This summing results in the loss of spatial and temporal information for individual photons. Other information could take many forms, such as, for example, spectral or energy level.

Various system and method embodiments disclosed herein are called "Discrete Event Detection Sampling," or "DEDS," systems and methods. DEDS encompasses "REDS" or "Radiant Event Detection Sampling" and "PEDS" or "Photon Event Detection Sampling," the latter being an appropriate designation whenever the radiant events involve photons. DEDS encompasses methods for producing imagable data on discrete events associated with a specimen. Events that are "associated with" a specimen include events that originate from the specimen or result from an interaction with the specimen. The discrete events can be, by way of example and not intended to be limiting, respective photons or groups of photons, respective units of radiation, and/or respective particles or groups of particles. Individual discrete events are detected during an image-acquisition period and are assigned a respective position indicating their site of origin in or on the specimen being imaged. The positions (e.g., x- and y-positions) can be obtained from position signals indicating the specific site in or on the specimen at the instant the event is detected, or can be obtained from time-based signals indicating the location of the imaged sites. The positions obtained for events occurring during the acquisition period can be stored in, e.g., a file in a computer. During formation of the image, each relevant position is assigned a distribution determined by a probability-density function (PDF), which expresses the uncertainty associated with its determination.

The respective distributions for the detected events are summed to form the image. The most appropriate PDF may be calculated or measured empirically and is determined by, for example, the nature of the instrumentation used to elicit and/or detect the events, the methods used for obtaining the image, the properties of the specimen, and the nature of the discrete events involved.

DEDS can be implemented in both scanning and non-scanning formats. In Scanning DEDS (SDEDS) the specimen to be imaged is scanned by moving the specimen and/or a detector or detecting probe relative to each other. For example, in certain types of REDS methods, an interrogation beam (e.g., of photons or particles) and/or the specimen are moved relative to each other. During an image-acquisition period a signal designating the position of origin, within or on the specimen, of each detected event is recorded and assigned a PDF. Individual PDFs are summed to form an image.

Certain DEDS embodiments do not require scanning the specimen with interrogating energy (e.g., a beam of light or of electrons). These Non-Scanning DEDS (NSDEDS) embodiments desirably utilize detectors comprising multiple discrete detection units that are small in size relative to the size of the distribution assigned to the PDF. Thus, the respective positions of the origins of the discrete, detectable events can be placed accurately in the image. The individual discrete events detected by each detection unit during an image-acquisition period are counted and assigned an appropriate PDF. In NSDEDS the position of origin of a discrete event can be designated as the position of the individual detection unit.

DEDS also encompasses embodiments in which the discrete events arise either spontaneously or without the need for input of interrogating energy. In these embodiments the position information required for each discrete event desirably is derived from an element(s) of the detection pathway, such as moving the specimen relative to the detectors (e.g., using scan mirrors or moving a stage on which the specimen is placed), moving a detecting probe relative to the specimen, or by using a detector with unitary detection elements of small size. The distribution used for the PDF reflects, inter alia, the nature of the discrete events and the properties of the detection pathway. In contrast, when interrogation energy is used, the PDF can also reflect the manner in which the interrogation energy interacts with the specimen, as well as the nature of the discrete events caused by the interaction.

In view of these fundamental aspects of DEDS, the subject methods and apparatus are useful for various diverse types of imaging systems and are not limited to confocal systems such as, for example, point-scanning confocal microscopy systems. The subject methods and apparatus are also not limited to methods and systems employing excitation or interrogation energy. The methods and apparatus also can be used to form images with, for example, transmitted light produced by the specimen but not in response to an excitation beam or interrogation beam. Scan mirrors can be used for directing light from specific regions of a specimen through a pinhole to a detector, wherein relevant position information is obtained for the detected discrete events (e.g., photons). The methods and apparatus also are not limited to microscope-based detection systems.

In accordance with certain embodiments of the present invention, apparatus and methods are provided for use with a scanned specimen that emits photons or other form of radiation during image-acquisition periods in which the location, or site, of the origin of individual photons, or sets of photons, are determined and recorded. The locations of the sources of individual photons or sources of photons are acquired in a "pixel-less" manner to yield positional information for each detected photon. The locations of the origins of the photons are acquired with reference to a scan frame that may be defined as a single instance of a scan pattern.

In one embodiment the scanner traverses the scan pattern over an image-acquisition period. During each successive scan, the scanner may have the same location at the same elapsed time from the beginning of the image-acquisition period. Therefore, during a scan, a current x-y location of the scanner may have a one-to-one correspondence with a value of a signal associated with scan position. One such signal may be a value of input to a scan driver. Another such signal may be elapsed time from the beginning of a scan. By measuring elapsed time in relation to the beginning of an image-acquisition period, the position of the scanner may be determined. Another such signal may be values of position feedback from the scan device.

Elapsed time may also be measured from a time the scanner has a known location rather than the beginning of a scan. The time of occurrence of detection of each photon or other discrete event is registered. The location on the specimen from which a photon, for example, was emitted is inferred from the location of the scanner at the time at which the photon is detected.

Whenever data concerning position rather than data concerning time are used, the true position of a scanner desirably is tracked independently of whether the scanner is following a scan-command signal in a faithful manner. In this case, the scanner can be driven at a frequency that exceeds the linear range of its amplitude/phase-frequency relationships to obtain greater scanning velocities.

Certain embodiments measure each discrete-event position by a position function associated with the position. An exemplary position function is event-probability density. The event PDFs are summed, which can require fewer discrete events to converge to an ideal density distribution associated with an image feature than are required using conventional pixel-based binning methods. Consequently, a smaller number of discrete events may be counted to yield increased spatial resolution and a decreased uncertainty concerning the sites of origin of the detected discrete events. Sensitivity of measurement also can be improved. Since fewer discrete events need be detected for a given resolution, less excitation illumination of a specimen to produce the discrete events (e.g., emission of photons) is required than with conventional pixel-based binning methods. The technique thus can eliminate or reduce over-irradiation of specimens and its concomitant adverse effects.

In certain embodiments, image frames may be constructed by summing the spatial distribution of photons or other discrete events over any user-selected time period rather than the specific period of a pre-selected pixel or voxel. Images can be displayed in raster space after they are stored digitally. Consequently, any imprecision introduced by the display process need not adversely affect the precision of the collected data. The original precise location data remain available in the digital storage.

Since some embodiments can provide high resolution in scan location, these embodiments also can provide high resolution in photon, particle, or other discrete-event location. In one embodiment, photon location corresponds to an analog signal that is converted to a digital signal having a pre-selected number of bits. This number of bits can be selected so that the generated image can be based in effect on photon-location data having a number of bits corresponding to a resolution of several megapixels per image or more in display space. Quality of a displayed image is limited only by the quality of display apparatus and not by the quality of the data.

In other embodiments, intervals between detections of individual discrete events are recorded. Various points in time displaced by equal intervals may each correspond to a milepost location of a scan. A "milepost location" is a predetermined, known location in the scan that is reached at a specific time within the image-acquisition period. The location of detected events can be calculated by interpolation between the milepost locations. Discrete events are recorded at a rate that is dependent on the number of events detected. Scan-rate need not be limited by the number of detected events expected to be counted in order to achieve a particular intensity and signal-to-noise (S/N) ratio as is typical in the case of conventional pixel-based sampling.

Alternatively, a signal may be indicative of the x-y position of the scan. The signal can, for example, comprise a monotonically increasing dc signal, in which the amplitude of the signal corresponds to a position of a scanned beam. A detector-output indicative of detection of a discrete event in one form triggers a sample-and-hold circuit to store the amplitude. The stored amplitude can be recorded. The amplitude can be converted to a corresponding digital value indicative of the precise location of the center of the beam (the location having a maximum likelihood of generating the detected event). A signal can be generated that is indicative of the time of detection of a discrete event and used to determine event location. Other techniques for determining the position of the scan may be used, including use of a clock or a counter activated from the beginning of the scan or other milestone.

For further precision, in certain embodiments the effect of various possibly interfering phenomena may be reduced or eliminated. These phenomena can include sampling delays that may occur in the acquisition of x-y position information and discrete-event detection, and differences between the positions indicated by the signal indicative of scanner positions and actual scanner positions. Examples of other such phenomena include the result of inertia of a scanning element or torque in an arm that rotates to drive a scanning component. Torque can result in different angular positions of opposite ends of a drive arm. By taking these types of phenomena into account, precision may be even further improved in certain embodiments.

In some embodiments, discrete-event counting may take place at high scan rates without the need to account for the number of event counts in a specimen. Image frames in raster space can be generated after the counts are registered and location data are stored. Using a single data set, dynamic events can be viewed to observe changes occurring over time by comparing images formed from sequential sample frames. Alternatively, discrete events (especially of a dynamic nature) can be viewed statically on different time scales.

Availability of complete sets of data in time and space can enable further forms of processing of the data, including post-hoc analysis, irrespective of acquisition time. Post-hoc analysis of the data can allow further analysis of the specimen, even after the specimen has become either unavailable or unresponsive to further excitation radiation.

In some embodiments, since multiple discrete events are acquired and statistical approaches are used to determine spatial locations of event clusters, measurement is not limited by the diffraction limit, such as defined by the Rayleigh criterion ($0.6\lambda/NA$) inherent in optical measurements. Consequently, certain embodiments can provide finer resolution than available from conventional imaging apparatus in which the resolution is limited by the diffraction limit.

It will be apparent from the foregoing that DEDS, REDS, and PEDS provide certain advantages over conventional pixel-based binning methods. These include: (a) since fewer discrete events are required to achieve the same S/N ratio as conventionally, the diameter of a pinhole (if used) upstream of the event detector can be decreased to improve optical sectioning further; (b) greater scan-rates can be used with the same intensity of excitation radiation, if used; (c) equivalent scan-rates can be used with a reduced intensity of excitation radiation, if used; (d) with the same intensity of excitation radiation, if used, a greater number of scans can be averaged to increase the S/N ratio of the image; (e) the centroid position of a specimen can be determined to a sub-diffraction limit more rapidly since fewer detected events (e.g., photons) are required; (f) more efficient image formation requiring fewer detected events (e.g., photons) results in decreased photo-bleaching and photo-toxicity of the specimen; and (g) generally any time an increased S/N ratio is beneficial.

The foregoing is a brief summary of characteristics of certain embodiments of the present invention. This Summary is not exhaustive; additional features and advantages of various embodiments will become apparent as this specification proceeds. In addition, it is to be understood that embodiments of the invention need not necessarily address all issues noted in the Background nor include all features or advantages noted in this Summary or in the balance of this specification.

BRIEF DESCRIPTION OF THE DRAWINGS

FIG. 3 consists of FIGS. 3(a) and 3(b), in which FIG. 3(a) illustrates photons that have been detected and their positions mapped in one degree of freedom, and FIG. 3(b) illustrates an exemplary sum of probability-density functions (PDFs) of the photons in FIG. 3(a).

FIG. 4 consists of FIGS. 4(a) and 4(b), in which FIG. 4(a) illustrates photons that have been detected as being associated with an image feature, and FIG. 4(b) represents an exemplary summation of the PDFs of the positions of the photons of FIG. 4(a).

DETAILED DESCRIPTION OF THE PREFERRED EMBODIMENTS

Figure 1:
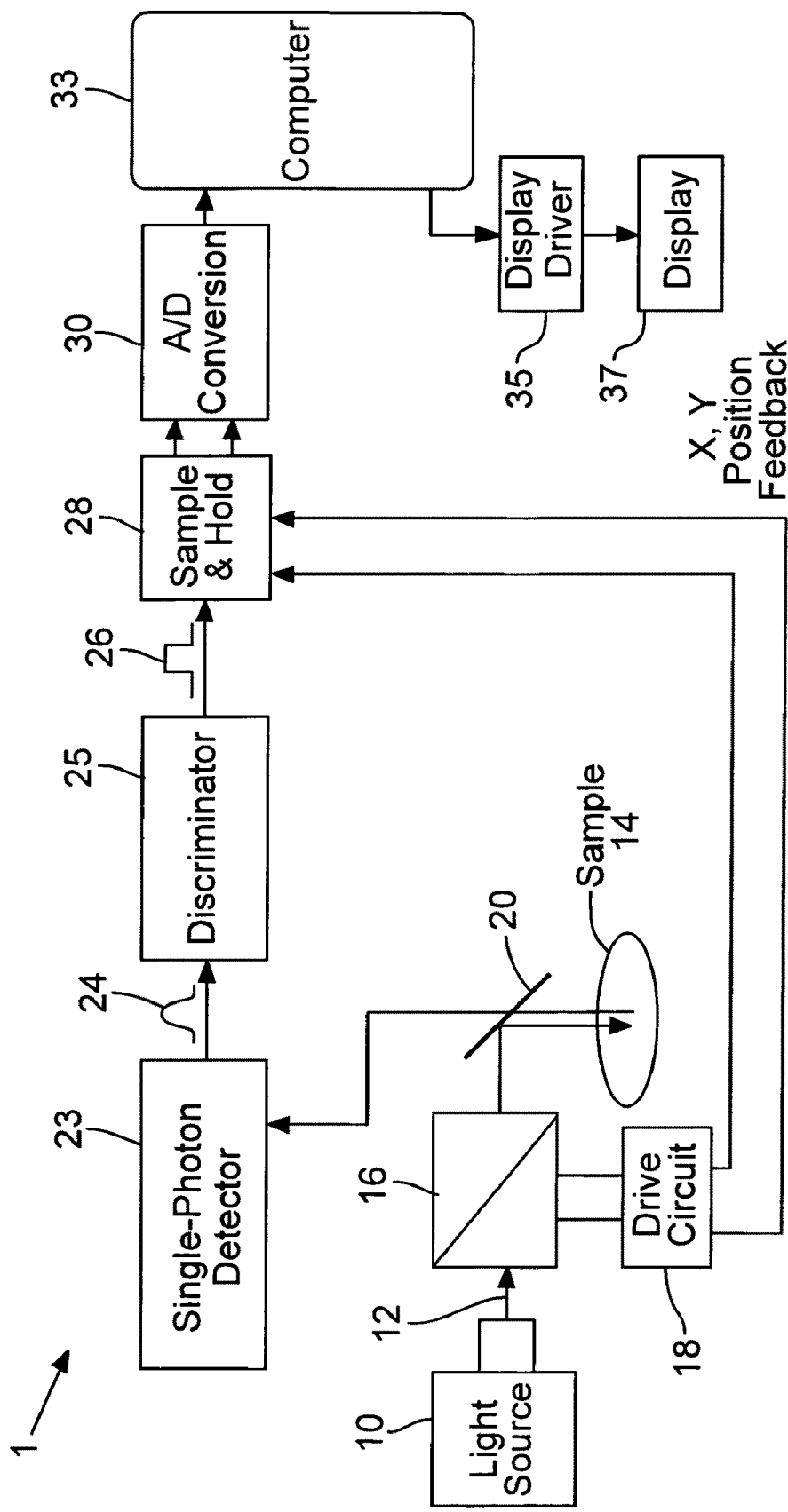
FIG. 1 is a block diagram of an apparatus, according to the first representative embodiment, in which signals indicative of scan positions are produced as photon events are detected. The photon events are stimulated by radiating the specimen using a laser beam.

The following disclosure is set forth in the context of representative embodiments that are not intended to be limiting in any way.

Discrete Event Detection and Sampling

Various system and method embodiments within the scope of this disclosure are generally called "Discrete Event Detection Sampling," or "DEDS," systems and methods. A fundamental aspect of DEDS is the use of a probability-density function (PDF) to describe the uncertainty associated with position attributed to any signal used to form an image. Such signals can be, for example, a detected photon or other unit of radiation, such as particle radiation (e.g., electrons). But, DEDS is not limited to applications involving elementary particles such as photons or electrons; DEDS can also be used when images are formed with signals generated in ways other than photons or particle radiation. For example, DEDS is applicable to methods in which discrete measurements (which can correspond to respective discrete events) are assigned respective positions of origin and these position coordinates are used to form an image. In these cases, application of a PDF describing the uncertainty associated with the position locations and/or the measured values themselves would be useful in a manner similar to the way in which such data are useful when images are formed using discrete events. In a general sense, these discrete measurements are regarded as discrete "events."

As noted, DEDS encompasses measurement of radiant events involving photons (PEDS) as well as radiant events involving non-photonic radiation (REDS), such as radiation of elementary particles or the like from a specimen. Examples of particles include, but are not limited to, electrons and alpha particles. In PEDS the photons are not limited to visible-light photons.

In DEDS the position of origin of each detected event in or on a specimen being imaged is convolved with a PDF related to an uncertainty associated with determining the position of origin of the event. The PDFs assigned to the discrete events detected during an image-acquisition period are summed to form the image. The distribution assigned to the PDF is determined by the properties of the events and by the characteristics of the instrumentation used to elicit and/or detect the events.

DEDS can be implemented in both scanning and non-scanning formats. In Scanning DEDS (SDEDS) the specimen to be imaged is scanned by moving the specimen and/or a detector or detecting probe relative to each other, or by moving an interrogation beam of radiation and/or the specimen relative to each other. During an image-acquisition period a signal designating the position of origin, within or on the specimen, of each detected discrete event is recorded and assigned an appropriate PDF. The individual PDFs are summed to form an image.

Certain DEDS embodiments do not require scanning the specimen with interrogating energy (e.g., a beam of light or of electrons). These Non-Scanning DEDS (NSDEDS) embodiments desirably utilize detectors comprising multiple discrete detection units that are small in size relative to the size of the distribution assigned to the PDF. Thus, the respective positions of the origins of the discrete events can be placed accurately in the image. The individual events detected by each detection unit during an image-acquisition period are counted and assigned an appropriate PDF. In NSDEDS the position of origin of a discrete event can be designated as the position of the individual detection unit.

DEDS also encompasses embodiments in which discrete events arise either spontaneously or without the need for input of interrogating energy. In these embodiments the position information required for each discrete event desirably is derived from an element(s) of the detection pathway, such as moving the specimen relative to the detectors (e.g., using scan mirrors or moving a stage on which the specimen is placed), moving a detecting probe relative to the specimen, or by using a detector with unitary detection elements of small size. The distribution used for the PDF desirably reflects the nature of the events and the properties of the detection pathway. In contrast, when interrogation energy is used, the distribution desirably reflects the manner in which the interrogation energy interacted with the specimen, as well as the nature of the discrete events resulting from the interrogation.

The full advantages of DEDS are realized when a distribution that is optimized for the properties of the specific imaging system being utilized is used to describe the PDF applied to the position of origin of each detected discrete event. The distribution describes the relative probability that a discrete event arose from a specified region in or on the specimen and permits the most accurate representation, in the image, of the position of origin and the most efficient use of each event to form an image. For example, in PEDS, the distribution would be primarily determined by the properties of the point-spread function (PSF) of the excitation light at its point of focus in the specimen. However, as noted above, a number of factors may influence either the interaction of energy with the specimen and/or the detection of consequential discrete events by a detector. Consequently, an optimum distribution desirably is determined for each type of imaging system and specimen.

DEDS can be used to form images more efficiently using scanning techniques that are not restricted to confocal microscopy, such as NSOM (near-field scanning optical microscopy), stage-scanning, etc. DEDS can be used for any electromagnetic radiation detected using optical or non-optical techniques. Hence, DEDS (and PEDS) is not limited to photons of visible light or even to photons of infrared and ultraviolet light.

The ability to converge more rapidly or with fewer discrete events and to eliminate one of the sources of error within the convergence (the limited resolution of a pixel or voxel) is a major advantage of the subject systems and methods. For example, the maximum likelihood position of two or more fluorophores separated from each other by less than the diffraction limit can be determined rapidly using PEDS or other DEDS method in which the wavelength or energy of individual photons is classified.

Probability-Density Functions

Various method embodiments as disclosed herein include obtaining, in an image-acquisition period and for each detected discrete event, respective location data and determining, from the location data, corresponding origin locations of the detected events in the image-acquisition period. The determined origin locations are convolved with a probability-density function (PDF) to produce a set of imagable data. The PDF describes the uncertainty associated with assigning a position as the site of origin of each event. The PDF can be a two-dimensional distribution or a three-dimensional distribution (the latter can be abbreviated "PSF"). PSFs are useful in three-dimensional applications of PEDS or DEDS.

Thus, not only are PDFs used, but it is advantageous that the applied PDFs be optimized. This involves applying an optimal PDF to individual discrete events, e.g., in PEDS to each photon detected. This also involves how individual PDFs applied to respective events can be summed in regions of overlap, of individual PDFs, to form an image.

With respect to applying an optimum PDF to each detected event, the distribution used usually will depend on the instrumentation utilized and the nature of the discrete event. As an example, for an embodiment configured as a laser-scanning confocal microscope (LSCM), an optimum PDF applied to each detected photon would be described primarily by the intensity distribution assumed by the excitation light at its point of diffraction-limited focus in or on the specimen. This is termed the excitation point spread function ($PSF_{Ex}$). Typically, $PSF_{Ex}$ can be approximated by a Gaussian distribution having a full-width at half maximum (FWHM) value similar to the spatial resolution of the optical system being used. By way of example, based on a Fraunhofer-diffraction approach, a diffraction-limited PSF can be calculated in terms of a first-order Bessel function, $J_1$, where the intensity profile is $(2J_1(s)/s)^2$ where $s=k\omega D/2$. Meinhart and Wereley, *Meas. Sci. Technol.* 14:1047-1053, 2003. In this case k is the wavenumber, $\omega$ is angular frequency, and D is the diameter of the aperture. Alternatively, the $PSF_{Ex}$ can be determined empirically for a given LSCM or other optical system. The use of these distributions to describe the PDF assumes a linear relationship between the intensity of excitation radiation and the probability of exciting production of a photon from incidence of the radiation on the specimen. For example, if fluorescent molecules having a non-linear relationship were used in association with the specimen, then an empirically determined PDF can be used, based on the nature of the non-linearity involved.

Different PDFs can be used for photons or other discrete events originating from different regions of the specimen if it were shown that the $PSF_{Ex}$ had different distributions in these regions. For example, this could arise due to optical aberrations present in the optical system. In some cases a $PSF_{Ex}$ can be calculated as described by Hell and Stelzer, Ch. 20 in Pawley (Ed.), *Handbook of Biological Confocal Microscopy*, 2nd Ed., Plenum Press, New York, 1995. Alternatively, the $PSF_{Ex}$ of an optical system such as an LSCM can be measured empirically as described by Rhodes et al., *Optics Comm.* 145:9-14, 1998, and Rhodes et al., *J. Opt. Soc. Am. A* 19:1689-1693, 2002. If desired, the PSF of an LSCM system or other optical system can be measured as described by Hiraoka et al., *Biophys. J.* 57:325-333, 1990. The latter may be used in cases in which light is emitted from a specimen in the absence of an interrogating light source.

In the second case, summation of the PDFs applied to individual detected events desirably is convolved as a function of the number of events detected. Again, using an LSCM system and PEDS as examples, as an increasing number of photons are detected, photon statistics (Poisson statistics) permit a more precise localization of the site of the origin or centroid of clustered events (i.e., a structure). Thus, as more events are detected, the distribution used for a summed PDF will begin to narrow from that of the Gaussian based on the $PSF_{Ex}$ used for a single event to a narrower Gaussian. With more events being detected from the same site of origin or from closely clustered sites of origin, there will be a further increase in the certainty of the locations; i.e., the ideal distribution used for a summed PDF narrows, where triangular waveforms provide a good approximation within a typical range used for fluorescent imaging, for example. Ultimately, as greater numbers of events are detected, the summed distribution assumes a delta function. Importantly, this statistical implication is the basis for PEDS methods that place the precise position of individual fluorescent molecules or of clusters of fluorescent molecules at much less than the spatial resolution dictated by the limits of diffraction. It is expected that localization accuracy achievable with PEDS and other DEDS methods will be on the order of a nanometer or less, or on the order of a few Ångstroms.

In many embodiments for PSF distributions applied to individual discrete events determined as described above, appropriate equations are applied to the PDF given to each event by routines in software being used to form the image, i.e., in a computer. In the case described above involving summed distributions, some flexibility can be applied to the task of making a transition from a "standard" Gaussian distribution based on a $PSF_{Ex}$ applied to each detected event to an optimal summation of these individual PDFs in regions of overlap, based on the "best" application of the particular statistical method that is used (e.g., Poisson statistics). The particular summing process used impacts the achievable efficiency of image formation with DEDS process under different conditions and with different types of specimens.

With REDS embodiments that involve non-photonic radiation, it is pointed out that elementary particles such as electrons exhibit properties of both particles and waves. Hence, a wave-based distribution function (a PDF) can be applied to imagable data collected using electrons. The data can be obtained using, for example, electron-microscopy methods, such as transmission or scanning electron microscopy. Recent innovations in these techniques have permitted application of electron microscopy techniques to living biological specimens.

First Representative Embodiment

This embodiment is a PEDS embodiment in which an image of a specimen being scanned by illumination light is formed by recording the x- and y-coordinates of the position of each transmitted photon (either fluorescent or reflected) from the specimen that reach a detector. These coordinates are obtained from position-feedback signals available from closed-loop scanners (e.g., galvanometers) used for scanning the illumination light. A probability-density function (PDF) is used to describe the likelihood that a detected photon came from a region in the vicinity of its actual position.

One way to formulate and optimize the region described by the PDF is to base the size and shape of the region on the size and shape of the illumination light at its point of focus in the specimen. The size and shape of the focused illumination light is described by the excitation point-spread function ($PSF_{Ex}$) of the optical system. See Cogswell and Larkin, Ch. 8, in Pawley (Ed.), *Handbook of Biological Confocal Microscopy*, $2^{nd}$ Ed., pp. 127-137, 1998. As discussed earlier above, a typical PSF assumes a more or less Gaussian distribution, and the full width at half maximum (FWHM) of this distribution approximates the diffraction-limited resolution achievable with a microscope system. Although other variations are possible, in a typical application of PEDS, the PDF assigned to the position of each detected photon is given a Gaussian distribution having an arbitrary unit amplitude and the same FWHM value as either the measured or the calculated PSF of the microscope system being utilized.

With reference to FIG. 1, a system 1, configured in accordance with this embodiment, is illustrated. A light source 10, generally a laser, provides a light beam 12 to illuminate a specimen 14. Light from the beam 12 is scanned across the specimen 14 by an x-y scanner 16. The x-y scanner 16 provides a scan pattern which may be a periodic linearly repetitive scan (e.g., repetitive row-by-row scan), a periodic non-linearly repetitive scan (e.g., repetitive spiral scan), or other scan pattern. During an image-acquisition period, the scanner 16 scans the light beam 12 in a scan frame over a selected region of the specimen (which can be the entire specimen or a portion thereof). The term "scan frame" is used to distinguish the subject frame from an image frame comprising pixels of a sensor that are illuminated simultaneously. In alternative embodiments, the scanner 16 is an x-y-z scanner.

The scanner 16 is driven by command signals from a drive circuit 18. The scanner 16 can be any of various devices useful for directing light in a scan pattern. An example scanner is a galvanometer scanner that directs rotation of a mirror to direct the light beam. An x-y scanner directs the light in first and second degrees of freedom, and to such end usually comprises two galvanometers and two mirrors. Other useful types of scanners include, but are not limited to, piezo-actuated scanners, acousto-optical scanners, and MEMS-based scanners (micro-electromechanical systems). MEMS-based scanners employ, for example, arrays of tip/tilt micro-mirrors. Command signals from the drive circuit 18 include respective signals for each instantaneous point in the scan frame; thus, the drive circuit 18 controls direction of the light by the scanner 16 to the instantaneous points in the scan frame at the proper respective instants in time. Not intending to be limiting, in one embodiment the scanner 16 is a non-linearly repetitive scanner as described in co-pending U.S. patent application Ser. No. 10/795,205, filed Mar. 4, 2004, entitled "Method and Apparatus for Imaging Using Continuous Non-Raster Patterns," published as U.S. Patent Application No. 2004/0217270, on Nov. 4, 2004, both incorporated herein by reference in their entirety.

In the depicted embodiment a dichroic mirror 20 reflects the light beam 12 from the scanner 16 to the specimen 14. The dichroic mirror 20 also passes light emitted from the specimen 14 to a detector 23. Although any of various detectors can be used, the detector 23 in FIG. 1 is a single-photon detector comprising, for example, a photomultiplier tube, an avalanche photo-diode, or an avalanche photo-diode array. Avalanche photo-diode arrays reduce well-known adverse effects due to dead time inherent in the response of an avalanche photo-diode. The distribution in space of each detected photon is approximated based on a point-spread function (PSF) of the optical system embodied in the apparatus.

The drive circuit 18 produces command signals each having a respective value uniquely associated with a respective position within a scan frame during an image-acquisition period. This value may be, for example, selected from a monotonically increasing dc value as the scanner 16 progresses through the scan pattern.

Whenever a photon is detected by the detector 23, the detector 23 produces an output pulse 24 that is input to a discriminator 25. From this input, the discriminator 25 produces a square-wave output 26 that comprises a clear rising edge and falling edge and that is directed to a sample-and-hold circuit 28. The sample-and-hold circuit 28 can comprise, for example, an R-C (resistor-capacitor) circuit. Meanwhile, the sample-and-hold circuit 28 also receives corresponding position signals from the drive circuit 18. The position signals provide, for example, potential levels to the sample-and-hold circuit 28. Thus, the signals received by the sample-and-hold circuit 28 correspond to the actual location of the detected light, from the scanner, on or in the specimen being imaged. Voltage outputs from the sample-and-hold circuit 28 are converted to corresponding digital signals by an analog-to-digital converter (ADC) 30. Thus, each output of the sample-and-hold circuit 28 is a signal indicative of the respective position, in the scan frame, of each detected photon.

In this embodiment the computer 33, being programmed with routines used for forming an image, performs the calculations of individual PDFs applied to the photon events. The computer 33 also performs summing of the PDFs.

Digital outputs from the ADC 30 may be stored in a memory (not shown) of the computer 33. If the scanner 16 is following its command signals faithfully, the current position of the scan in the scan frame at which a photon is detected also correlates with a respective elapsed time since the beginning of the current image-acquisition period. In other words, a current x-y position, or x-y-z position, of the scanner 16 has a direct correspondence with a particular elapsed time from the beginning of the scan. Hence, an alternative signal indicative of the position, in the image-acquisition period, at which a photon is detected is a scan signal corresponding to the elapsed time from the beginning of the image-acquisition period. If appropriate, these time moments are registered by the computer 33. Thus, the respective time and position of each detected photon may be determined and registered.

The computer 33 also may be utilized to provide, from the position data, a respective time associated with each detected photon. Imprecision in the resolution and/or sample locations may be produced during the scan due, for example, to an inability of the scanner 16 to follow its command signals faithfully. These imprecisions can be corrected by the computer using position-feedback signals from the scanner 16 (see FIG. 1). The computer 33 may also be coupled to video circuitry to produce an image corresponding to these stored values of time and position. To such end, the values are provided to a video-display driver 35 to produce the image on a display 37. Also, using the computer 33, it is possible to overlay the image of the scanned region with an image produced by a video camera or the like.

The location, or site, of the origin of every detected photon contributing to the image is determined, and the respective times at which the photons are detected may be recorded if desired. The locations of the sources of individual photons are acquired with reference to positions of corresponding photons in the scan frame without, in contrast to conventional apparatus, reference to physically defined pixels. The location from which a photon was sensed is the location at which the scanner was directed at the moment the photon was sensed. While it can be desirable to sense every photon to obtain the maximum amount of information concerning the specimen for a given amount of input illumination, images can be generated in accordance with embodiments of the present invention if fewer than all photons are sensed or if groups of photons are sensed within a given image-acquisition period of a given scan area.

PEDS can be used for both single-photon excitation confocal imaging as well as multi-photon excitation applications. Also, in the latter application, PEDS can be used with both descanned and non-descanned modes of detection.

Second Representative Embodiment

Figure 2:
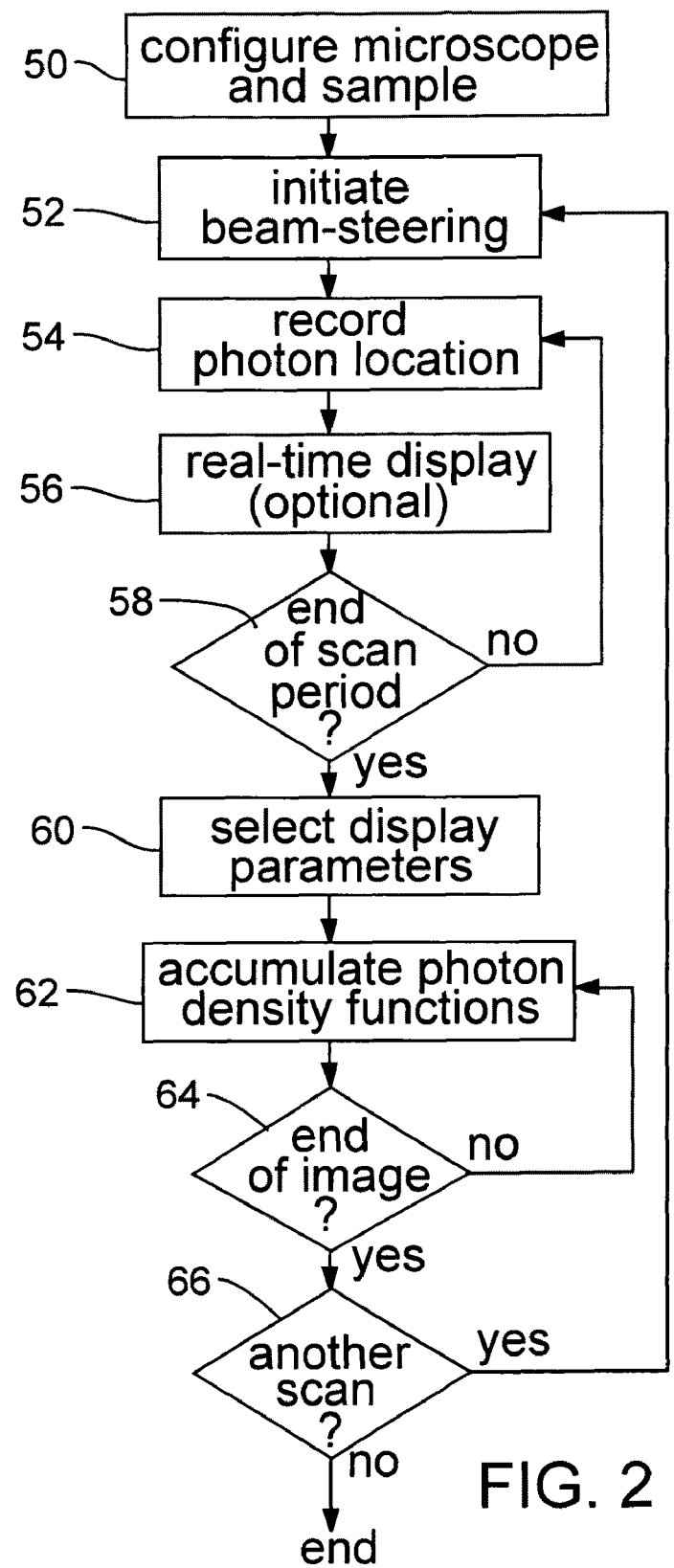
FIG. 2 is a flow diagram of an embodiment of a method that can be performed using the apparatus shown in FIG. 1.

With reference to FIG. 2, an embodiment of a method for determining photon location and producing an image comprises a step 50 in which an operator places the specimen 14 in the microscope system 1. In the step 52, scanning of the light beam 12 over the specimen 14 is initiated. Respective photon locations are recorded (54) if and when photons are detected by the single-photon detector 23. A display of position information 56 may then be provided at the display 37. If a "scan period" (image-acquisition period) is not complete 58, operation continues, and detected photons will again have their respective locations recorded 54. After the scan period, operation proceeds for further data processing, including a decision (58) as to whether the scan period is ended or not.

If the scan period has ended, display parameters, e.g., raster locations, are selected 60 to provide a framework so that recorded photon locations in non-raster space can be mapped into raster images on the display 37. Display parameters can include a grey or color-based scale for displaying density functions. Mapping is advantageous since the recorded data typically has a finer resolution than the pixels within the raster. In other embodiments, in which scans are also made at successive depths in the specimen 14, a set of sample data can be mapped into three-dimensional voxel space. Respective probability-density functions (PDFs) are accumulated (summed) 62. The PDFs may be summed by, for example, a distributive or an associative method. In the associative method, an intensity value is calculated based on distances to a number n of nearest photons for each pixel. In the distributive method, each photon record is accessed and mapped into one or more raster locations. In this method, both the x- and y-locations can be sampled to a high degree of precision. Therefore, the respective PDF of a single photon in one display pixel can make fractional contributions to one or more other pixels. In one embodiment, the locations are sampled with 12-bit resolution. This level of resolution on one axis yields a two-dimensional image resolution of $2^{12} \times 2^{12} = 16$ megapixels. This level of image resolution may be described as a 16-megapixel raster space. The accumulation of photon-density functions continues until processing of an image of the scan is completed 64. Another scan may be initiated 66, or the operation may be completed.

Figure 3:
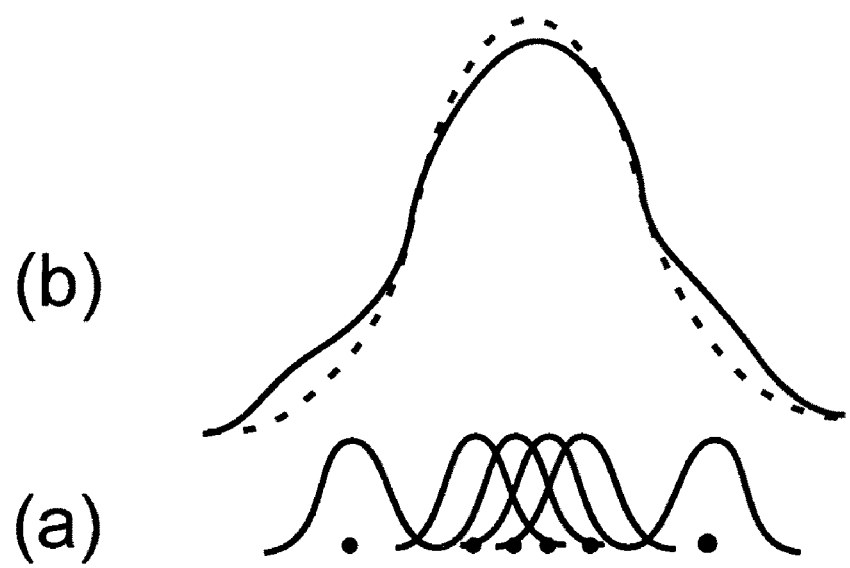
Figure 4:
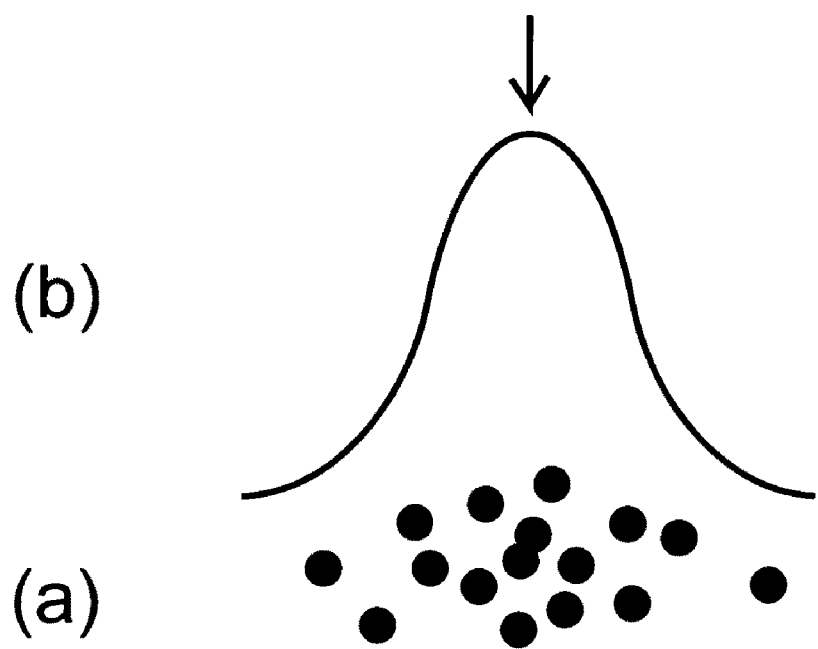

FIGS. 3 and 4 are illustrations of sensed photons and their associated PDFs. FIG. 3 consists of FIGS. 3(a) and 3(b). In FIG. 3(a) solid circles represent respective single photons that have been detected and that have had their respective positions determined by one degree of freedom. Associated with each photon is a PDF. The horizontal extent of FIG. 3(a) defines a region that could, for example, correspond to a display pixel. Summing these PDFs yields the solid curve in FIG. 3(b). Summing of photon PDFs causes the solid curve to converge to an ideal distribution curve represented by the dashed curve. This summing of PDFs requires fewer photons to converge to the ideal density distribution associated with an image feature than are required using conventional photon binning. As a result, certain embodiments permit images to be formed more efficiently than by other embodiments or than conventional devices.

FIG. 4 consists of FIGS. 4(a) and 4(b). In FIG. 4(a), solid circles represent photons that have been detected and that are associated with an image feature. FIG. 4(b) represents a summation of the PDFs of the positions of the photons of FIG. 4(a). The center of the curve in FIG. 4(b), indicated by an arrow, represents the central location of the image feature as determined from the summation.

The resolution of the central position obtained in this statistical manner is less than the diffraction limit of light (0.6λ/NA). This physical limit is thus overcome by certain embodiments of the present invention.

Third Representative Embodiment

Figure 5:
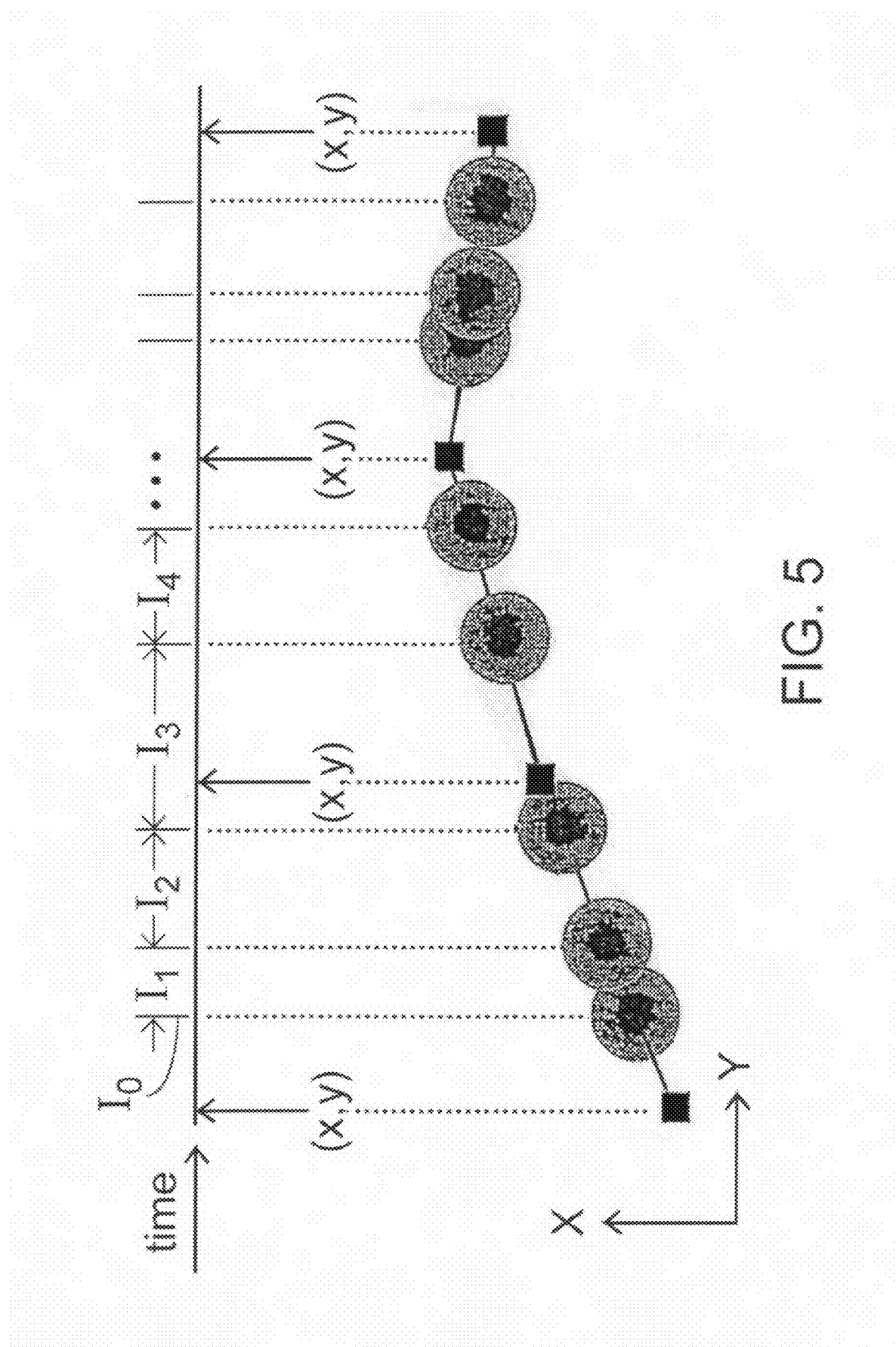
FIG. 5 is an illustration of data collected in an embodiment in which time intervals between pulses are measured in order to determine locations of corresponding photons.

FIG. 5 is an illustration of data collected in an embodiment in which time intervals between pulses are measured to determine locations of corresponding photons. Data may be collected using, for example, the apparatus of FIG. 1. However, rather than having the sample-and-hold circuit 28 store a potential level in response to each square wave 26, a pulse output indicating time of production of the square wave 26 is produced. The apparatus of also produces periodic "milepost" pulses having constant inter-pulse intervals. The milepost pulses can be produced by, for example, a clock or a constant-frequency oscillator. Each milepost pulse corresponds to a known position of a scanning beam in the scan pattern of the scanner 16.

In FIG. 5 the horizontal axis represents time. The curve plotted in x-y coordinates indicates the path of the scanning beam. In the present example, the scanning pattern comprises a spiral path. See U.S. Patent Application No. 2004/0217270, published on Nov. 4, 2004, incorporated herein by reference in its entirety. The solid dots represent respective locations from which single photons are received, and the circles surrounding each dot represent the point-spread function inherent in the optical system of the confocal microscope system 1. The squares represent milepost beam locations. Each point in time during a scan has a unique corresponding x-y position. The position of the scan at the instant of each milestone pulse is known. In the present example, photon detection pulses are produced, for example, after intervals $I_0$, $I_1$, $I_2$, $I_3$, and $I_4$. The computer 33 performs linear interpolation to determine the respective location of each detected photon. In this example, interpolation is performed between the times of the consecutive milepost beam locations flanking a particular interval. Interpolations can also be performed between other pairs of milepost beam locations flanking any of the intervals $I_0$, $I_1$, $I_2$, $I_3$, and $I_4$. In another alternative configuration, a plurality of interpolations may be performed respectively between each of multiple pairs of beam mileposts. The results of the interpolations can be averaged or otherwise processed. Based on PDFs, an estimate of the spatial distribution is made to generate images as described above.

Certain embodiments can thus provide for measurement of the actual locations of detected photons. Once the locations are measured, precise values indicative of the locations can be stored. A stored set of location data in time and space is thus provided for later recall and further processing, if desired. Hence, it is not necessary to repeat an experiment to use different measurement parameters with the data. Locations can be determined to a far greater degree of precision than is available in currently available display techniques. The precision is not limited by the physical diffraction limit inherent in optical measurements because image frames are constructed by summing photon PDFs. This requires fewer photons to converge to an ideal density distribution associated with a feature image than are required using conventional pixel binning. The resulting increased sensitivity exhibited by embodiments of the present invention permits reduction or elimination of adverse effects of over-illumination of specimens.

Devices, such as a quad-cell photodetector, capacitance (eddy-current) sensor, or the like, can be used to improve the accuracy and precision of assigning respective positions to the photons. Mechanical accuracy is not limited by any of sort of diffraction limit or other foundational limit down to molecular scales and, as such, can be measured accurately in a number of different ways.

The data obtained as described above may be processed in a number of different ways. For example, the data can be rendered in a histogram format for commonly used analyses, such as fluorescence-correlation spectroscopy. Alternatively, an interval clock, relative to the timing of a pulsed laser, can be triggered by photon detection during data acquisition, and fluorescence lifetimes can be analyzed. In another variation, detected photons can be categorized according to their energy content and assigned an appropriate distinguishing color. In addition, it is possible to temporally expand and/or contract a data set acquired during a single high-speed acquisition period. Consequently, flexibility is provided in extracting kinetic information concerning the dynamics of the process being imaged over any relevant time scale.

In some embodiments, repeated scans of a specimen allow for comparison of one scan to another, and corresponding elements of one scan to another. The scans may be consecutive or non-consecutive, and the elements may be images, portions of images, or photons or sets of photons. Alternatively, positions of photons measured over integrated groups of image-acquisition periods may be compared. With appropriate compensation for noise and thermal expansion, movements in the sub-nanometer range may be detected.

Once a data set of positions of origins of photons has been acquired, the set can be used to cast the data in any time frame or to apply different PDFs, etc., as desired. Thus, the data set can be manipulated in a wide a manner as other types of data sets, especially with the availability of a many types of computers and computer software.

Figure 6:
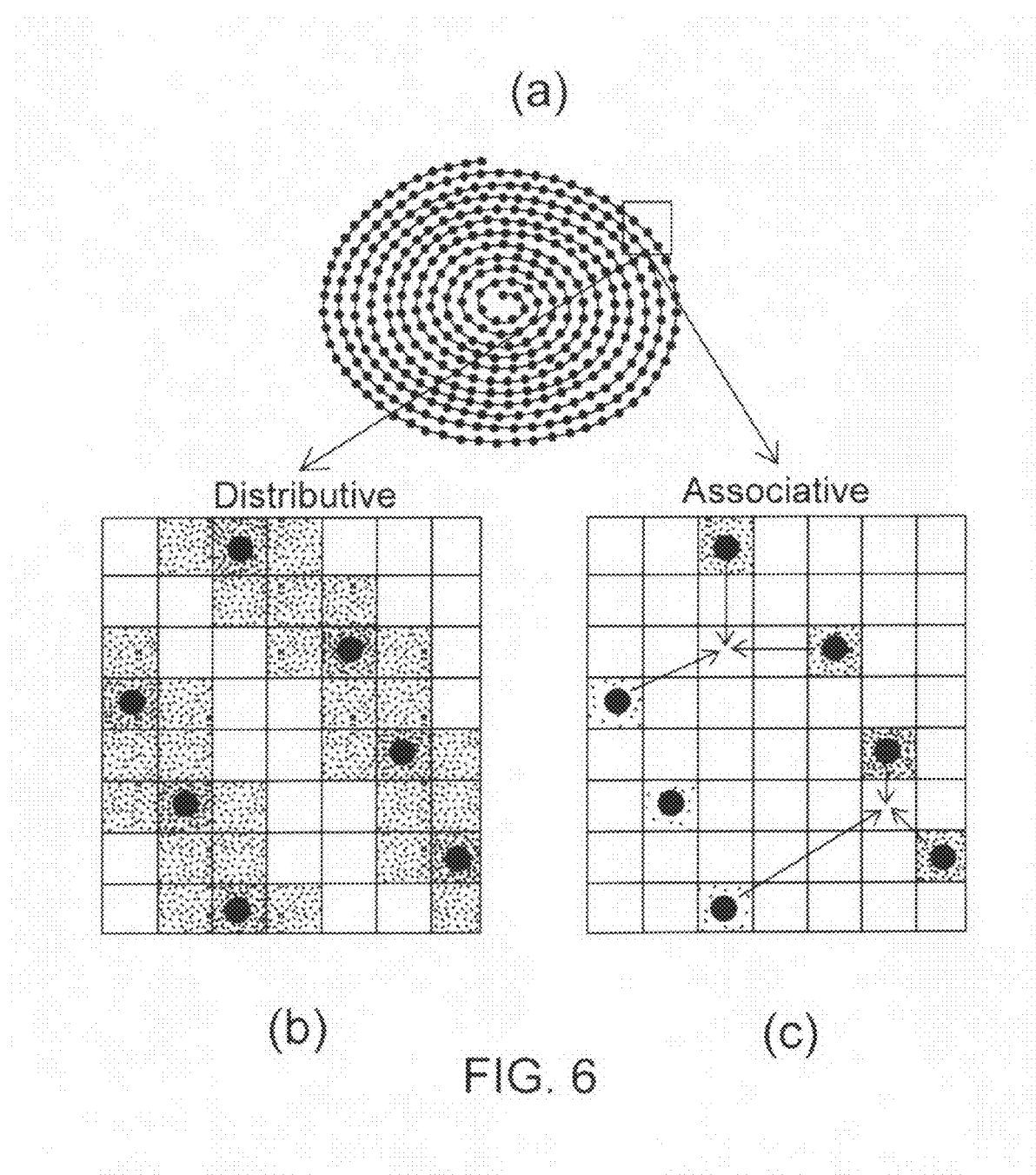
FIG. 6, consisting of FIGS. 6(a), 6(b) and 6(c), illustrates mapping of sensed positions into display raster space.

Another use of the photon-detection data is to produce an image on a display or the like. Photon-position data is determined to a high degree of resolution and stored (e.g., in memory of the computer). To produce a display of the data, the recorded positions of photons may be mapped into the raster space of a display device. FIG. 6, consisting of FIGS. 6(a), 6(b), and 6(c), is useful in understanding embodiments of one method for mapping. FIG. 6(a) represents a non-raster scan (NRS) pattern, FIG. 6(b) depicts a "distributive" method of mapping, and FIG. 6(c) depicts an "associative" method of mapping.

With regard to the distributive method (FIG. 6(b)), "n" nearest two-dimensional raster display pixels are considered as pixels to which one photon scan location can be assigned. As in the associative method described below, the influence of each newly acquired sample on nearby raster pixels can be weighted to the distance between the location of the sample point and the location of the display pixel (e.g., inversely proportional to produce linear interpolation). In addition, the time since a pixel was last updated can be taken into account. Raster (i.e., grid) locations in the track of a spiral scan pattern (or other scan pattern) are assigned sampled-intensity values and weight factors. One suitable weight factor is inversely proportional to the distance from the actual scan path. Other functions of distance alternatively can be used. Raster-intensity values are then assigned based on the intensities/weights at each location or interpolated from neighboring pixels if no weights/intensities have been stored (a situation illustrated as white grids above). An advantage of this scheme is that most of the computation required for producing raster images can be performed one point at a time, as each sample is acquired. The distributive method usually requires more computational time and is better suited for producing a final raster-display image, once a complete non-raster sample set has been acquired.

In the associative method (FIG. 6(c)), the "n" nearest sampled (i.e., non-raster) points to each two-dimensional (raster) display pixel are found. By weighting non-raster sample points inversely proportionally to the distance between the location of the sample point and the location of the raster display pixel, it is possible to generate an accurate representation of non-raster data rapidly with smooth transitions in the raster-grid display. Each raster pixel is assigned a value based on an average intensity that is weighted. A weighting factor may be inversely proportional to the distance between the raster location and the spiral sample location. Other functions of distance can be used. In this example showing how the intensity values of two pixel locations (pointed to by the collection of arrows) are computed, three nearest spiral samples are used to make the calculation. In both schemes illustrated in FIGS. 6(b) and 6(c), relative weight factors are represented as grayscale intensity, where darker locations are weighted more heavily.

A significant advantage that can be achieved with either mapping method is that the number of non-raster samples can be independent of the number of raster-display pixels. Thus, if high temporal resolution (i.e., a high frame-rate) is desired, a small number of samples along a non-raster pattern can produce a roughly uniform distribution of samples along a raster or non-raster pattern. On the other hand, if high spatial resolution is desired, then more "spirals" can be selected. When tracking rapid dynamic behaviors or making comparisons with spatial-temporal mathematical models, the non-raster pattern can be used to select just enough spatial resolution while maximizing temporal resolution. The number of command points per image and frame rate can be chosen under software control to be any values on a continuous scale (i.e., points can be added or subtracted). Maximum values are governed only by sinusoidal scanning frequency and photon-detection efficiencies, not by the characteristics of display devices.

As an example of using a non-raster pattern with a NRS-LSCM, if each sample required a dwell time of 0.5 microseconds to gather a sufficient number of photons and if 2000 samples were needed for adequate spatial resolution, then a frame-rate of 0.5×2000=1000 frames/second could be achieved. Greater frame-acquisition rates can be chosen, under software control, without having to make any modifications to hardware. In these examples, a low number of spiral samples (e.g., 450 points along a spiral scan frame) in combination with a low ratio of spiral sample to raster pixel have intentionally been used to simplify illustration of the different mapping methods.

If desired, the highest possible scan rates can be used without consideration of the number of photons being acquired. After a complete data set has been acquired, raster-space images having desired intensity values can be constructed by combining one or more scan frames. Thus, using a single data set, a dynamic event can either be viewed to observe changes occurring over time by comparing respective images formed from sequential sample frames, or the event can be viewed statically on different time scales by combining data from more than one sample frame. In the latter case, the accuracy of parameters obtained for a dynamic event described at high temporal resolution by one or a few scan frames can be compared with those derived from images of the same event obtained over a longer interval. Useful information can thus be provided regarding the interval of scanning needed to obtain a given level of accuracy.

Storing of the data thus obtained allows for further use of the data. Frame images can be reconstructed and viewed at different temporal rates, thereby permitting compression or expansion of viewing of an overall data set. The availability of complete data sets in space and time makes it possible to conduct repeated post-hoc analyses rather than repeating an experiment using different measurement parameters. This saves cost and reduces inconvenience. Availability of post-hoc analysis guarantees that analysis may be made even when a specimen is no longer available or is no longer responsive to radiation excitation. This feature provides a number of advantages including the ability to: (i) compare conventional images using pixel "bins" with those accumulated using DEDS-based PDFs, and (ii) determine the exact sequence of photonic responses relative to other events. For example, a photon event can be related to an electronic or metabolic change in the specimen being imaged.

Another use of REDS/PEDS is to overcome prior-art limitations of scanning microscopes in achieving required spatial resolution and detail in producing an image of a biological specimen or inspecting properties of the surface of a material. Using prior-art scanning-microscope techniques usually involves the need to utilize microscope objectives, having high numerical aperture (NA), that require immersion in a fluid medium and that must be situated in close apposition to the specimen or surface to produce required spatial resolution and detail. To minimize specimen manipulation and increase throughput, however, it is advantageous to utilize lower-NA objectives having longer working distances that allow an air interface between the objective and the specimen or surface.

Fourth Representative Embodiment

Figure 7:
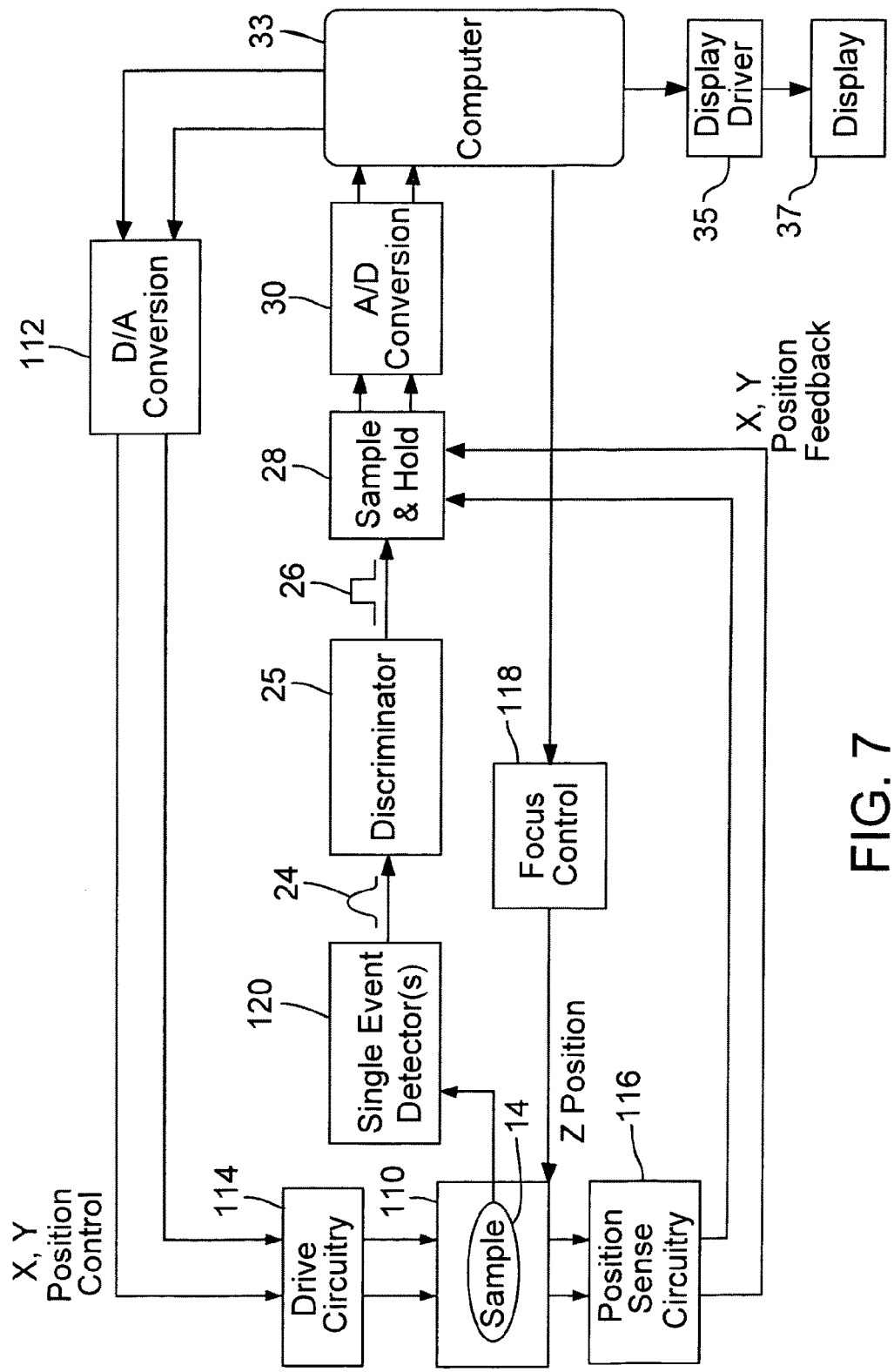
FIG. 7 is a block diagram of an apparatus embodiment, according to the fourth representative embodiment, that detects radiant events occurring in or on a specimen without having to expose the specimen to an interrogating or energizing beam.

This embodiment is similar in some respects to that of the first representative embodiment but does not involve a scanning or interrogating beam. This embodiment is illustrated in FIG. 7, in which components similar to those shown in FIG. 1 have the same respective reference numerals and are not described further.

The specimen 14 is positioned on a stage 110 or the like that is configured for motion in the x and y directions. X- and y-position control is provided by the computer 33. To such end, digital control signals from the computer 33 are converted to corresponding analog signals by a digital-to-analog converter (DAC) 112. The resulting analog signals for x- and y-position control are converted to corresponding stage-drive signals by drive circuitry 114. X- and y-position detection of the stage 110 is performed by position-sense circuitry 116 (e.g., encoders or interferometers), which provides x- and y-position feedback to the sample-and-hold circuit 28. For optimal detection of radiant events occurring on or in the specimen 14, the z-position of the stage 110 is controlled by a focus control 118 that receives appropriate control signals from the computer 33. Actual detection of radiant events is performed by at least one "single-event detector" 120, which routes corresponding detection pulses 24 to the discriminator circuit 25. The discriminator circuit 25 converts the detection pulses 24 to corresponding square-wave pulses 26 that are routed to the sample-and-hold circuit 28. Output from the sample-and-hold circuit 28 is converted to corresponding digital data by the ADC 30 and routed to the computer 33. In addition to its various computational tasks, the computer 33 also convolves PDFs to the data delivered from the ADC 30 and sums the PDFs to produce imagable data. The imagable data are routed to a display driver 35 and then to a display 37.

EXAMPLES

Example 1

This example is directed to the measurement of the release of calcium ion, $Ca^{2+}$, from intracellular sarcoplasmic reticulum (SR) stores in cardiac cells using an apparatus as disclosed above. $Ca^{2+}$-release activates contractions of the heart for pumping blood throughout the body. $Ca^{2+}$ is released through ryanodine receptor (RyR) $Ca^{2+}$ channels present in SR membranes. Information concerning the functional properties of these channels, as they exist inside heart cells, can help in understanding how contraction of the heart is activated and regulated. Since RyR channels are present in intracellular membranes, they cannot be studied using conventional microelectrode-based electrophysiological techniques. However, changes in intracellular $Ca^{2+}$ can be measured non-invasively by monitoring fluorescence of dyes, such as fluo-3, introduced into the cytoplasm of the cell. Fluorescence increases when $Ca^{2+}$ binds to the dye.

Small increases in fluo-3 fluorescence observed in cardiac cells, termed "$Ca^{2+}$ sparks," are thought to be due to release of $Ca^{2+}$ from a small number of RyR channels. A "$Ca^{2+}$ spark" represents a photon emitted by a calcium-sensitive fluorescent dye excited by a laser beam in the presence of calcium ions. $Ca^{2+}$ sparks may represent elemental events that are first steps in the activation of contractions in the heart. As such, they can provide information concerning the activity and properties of RyR channels in intact cardiac cells. A situation that complicates relating the properties of $Ca^{2+}$ sparks directly to activity of RyR channels is that spark properties can be influenced by conditions and factors within heart cells that are not related to the activity of RyR channels. These factors interact with one another and cannot be easily manipulated individually in intact cells. Thus, it has proven difficult to assess in a direct experimental manner how each factor and condition alters $Ca^{2+}$-spark properties. To date, workers in the field have attempted to use computer modeling and simulations to dissect influences by cellular factors and conditions from those related to the activity of RyR channels.

An alternative and complementary approach to this problem is an in vitro optical-bilayer system that permits imaging of fluo-3 fluorescence in response to $Ca^{2+}$ flux through single RyR channels reconstituted into artificial planar lipid-bilayer membranes simultaneously with electrical recording of single RyR-channel $Ca^{2+}$ currents. PEDS is advantageous for solving this because PEDS excels at permitting signals with low spatial frequencies to be imaged over small scan ranges in a more efficient manner.

Example 2

This example is of the system 1 of FIG. 1, configured as a confocal microscope. The microscope comprised a model MRC 600 laser-scanning confocal-microscope system (LSCM) from BioRad Laboratories, Hercules, Calif. The laser 10 was any of various ion-lasers or solid-state lasers emitting in the ultraviolet to infrared wavelengths. Examples are available from Melles Griot of Rochester, N.Y., and Blue Sky Research of Milpitas, Calif. The scanner 16 comprised an x-y steering device, including mirrors mounted on closed-loop galvanometers, available from Cambridge Technology, Inc., of Cambridge, Mass. A pair of Cambridge Technology Model 6800 closed-loop galvanometers was used, which can exhibit scan frequencies of 500-600 Hz over mechanical scan angles of ≦10°. These frequencies were determined for raster scanning (i.e., repeatedly starting and stopping). Scan frequencies of slightly greater than 1 kHz (limited by safeguard circuitry on the driver card) can be obtained using non-raster scanning and position-feedback signals to establish sample position in non-raster space.

The dichroic mirror 20 was obtained from Semrock, Inc., of Rochester, N.Y. The laser beam was focused onto a specimen or sample by a focusing device such as a microscope objective.

Movements of the beam-steering device and scanning of the radiation were dictated by command signals originating from a computer under software control and converted to appropriate analog voltages by a digital-to-analog converter (DAC). The DAC had a resolution dictated by the spatial-resolution requirements of the measurement being made, and was obtained from National Instruments, Austin, Tex. The beam-steering device was moved in either a raster pattern or in a non-raster pattern to scan the electromagnetic radiation across the specimen or sample. Photons, due to reflected or fluorescent light and originating from a focal plane in the specimen or sample, passed through the wavelength-selective device and were counted as single events by a single-event detector, in this example an avalanche photodiode obtained from Perkin Elmer Optoelectronics of Wellesley, Mass. Alternatively, a photomultiplier tube available from Hamamatsu Corporation of Bridgewater, N.J., operating in a single-photon-counting mode can be used. Single pulses were sent from the detector to a discriminator circuit for every photon detected.

The BioRad 600 LSCM can scan a single line in the x-dimension in ~2 msec. Therefore a full-frame x-y image containing 768×512 pixels (i.e., 512 t-line scans, with each line containing 768 pixels) could be obtained in ~1 sec. The rise-time of a $Ca^{2+}$ spark in a cardiac cell is ~8-12 msec. Consequently, using this system, only six points or less could be used to describe the onset of the spark event. Single-x, t-line scans were employed to achieve the highest scan-rates possible. In this approach, spatial sampling was collapsed to a single dimension, as the same line is scanned repeatedly as rapidly as possible.

Since $Ca^{2+}$ sparks are four-dimensional events occurring in x, y, and z spatial dimensions, as well as in time. Hence, spatial sampling and data interpretation sometimes were not optimal.

One reason for the limited temporal resolution of the MRC 600 in some LSCM systems is that mirrors mounted on separate closed-loop galvanometers (CLGs) are used to scan the laser beam in the x- and y-dimensions in a raster pattern. This requires that the laser beam be turned around at the beginning and end of each line, which involves stopping and starting a CLG. Since the shaft of a CLG has significant mass, and since relatively large mirrors are typically used to accommodate laser beams whose diameters have been expanded for optical reasons, considerable inertia is involved. The time required to reverse the direction of the laser beam is a significant portion of the time required to scan a single line, which imposes a fundamental limit on the scan rates that can be achieved. In addition, since pixel size in current LSCM systems is determined by the pixel clock interval, uniform sampling during a scan requires that the laser beam move at a constant velocity.

Thus, the time required for the CLG to accelerate to a constant velocity can also impact scanning capabilities.

Example 3

In this example the discriminator circuit (see item 25 in FIG. 1) was adjusted to separate pulses caused by photons from those caused by random noise. Each pulse generated by a photon resulted in a digital pulse being sent to the sample-and-hold circuit (see item 28 in FIG. 1). Each time a digital pulse was received, a corresponding set of voltages representing the x- and y-positions of the beam-steering device at the time the photon was detected were retained by the sample-and-hold circuit. The position signals from the beam-steering device were converted to digital signals and passed to the computer (item 33 in FIG. 1) by the analog-to-digital converter (ADC, item 30 in FIG. 1) having a resolution appropriate for the measurement being made. The ADC was obtained from National Instruments, Austin, Tex. The position of each photon detected within the image domain was transmitted via a display driver (item 35 in FIG. 1) to a display device, such as a computer monitor, to form an image of the illuminated region of the specimen or sample. The display utilized either a raster or non-raster scanning format.

The intensity value assigned to each photon in the spatial domain of the image could be adjusted as a probability-density function (PDF) formulated relative to the point-spread function (PSF) of the illuminating radiation and the probability of exciting emission from the excitation properties of a fluorophore positioned within the illumination PSF. The focal plane in the specimen or sample being illuminated by the electromagnetic radiation was selected under computer control via focus-control circuitry controlling the position in the z-axis at which the radiation is focused in the specimen or sample. (This control is currently typically implemented via a serial (USB) port interface with the focus-control circuitry.) As is the case with x- and y-position signals, voltage-indicated z-positions could also be passed via an ADC channel to the sample-and-hold circuit 28 and then to the computer 33. Algorithms commonly used to eliminate photons originating from above and below the focal plane can be used to enhance images obtained in this example.

The NRS-LSCM of this example offered particular advantages for imaging dynamic processes. Such dynamic processes include changes in intracellular $Ca^{2+}$ ($Ca^{2+}$ sparks and waves) involved in tissue activation and intracellular signaling, changes in membrane potential in excitable tissues (e.g., heart and brain), and the spread of activation within the GI tract. Images of these events, as well as of many other cellular processes, contain relatively low spatial frequencies. Therefore, relatively low sampling frequencies (and consequently high scan rates) can be used to establish their properties in an adequate manner. This example and other embodiments of the present invention can image events involving intermediate to low spatial frequencies at maximal possible (photon-limited) sampling rates. Because spatial-resolution capabilities are not sacrificed to obtain greater temporal resolution, the NRS-LSCM system provides a data-collection rate equal to the performance of systems for imaging specimens containing high spatial frequencies, where greater sampling rates (and lower scan speeds) are used.

Further examples below show that DEDS permits approximation of the true distribution of photons or other discrete events arising from a specimen more efficiently and with fewer photons than achieved using conventional pixel-based binning methods. This results, at least in part, from an increase in the signal-to-noise ratio (S/N ratio or SNR) of the image obtainable using DEDS. Two SNR values are commonly measured. An SNR value can be defined as the ratio of the signal, measured as the mean number of photons arising from the specimen ($signal_{spec}$) and the noise (standard deviation of the mean signal) present either in the signal obtained from the specimen ($noise_{spec}$) or in the signal obtained from a background (bkg) region not occupied by the specimen ($noise_{bkg}$). To compare the effects of DEDS and binning on both types of SNR, photon-event files were generated that contain the x- and y-position coordinates of each photon detected during an image frame.

Example 4

To permit direct comparison, PEDS and conventional binning processes were used in this example to form images from the same photon-event file. To assess conventional binning, a consensus optimal pixel size (FWHM of the PSF/2.3) was utilized. See Pawley, Chapter 4 of Pawley (Ed.), *Handbook of Biological Confocal Microscopy*, $3^{rd}$ Ed., pp. 59-79, 2006. A 60× oil-immersion objective having an NA of 1.45 was used to obtain images. A FWHM of 202 nm was calculated from the formula: $0.6\lambda/NA$ (where $\lambda$=488 nm, the excitation light wavelength). This yielded an optimal square pixel size with a lateral dimension of 88 nm. The area scanned in the specimen to generate the photon-event file was fit with an array of 88-nm pixels having an equal number of rows and columns. The number of photons present within each pixel was summed. The summed values were then used as intensity values to form an image.

For evaluation of PEDS, a PDF was applied to each photon position in the photon-event file. In this example the PDF was a Gaussian distribution, in which the area under the curve represents unity, the value given a discrete event prior to assignment of a PDF, so that the intensity represented by a single discrete event is not altered. The Gaussian distribution had an arbitrary unit amplitude of which the FWHM was equal to the 202-nm FWHM of the calculated PSF. Individual PDF values were summed in regions of overlap. The resulting values were used as intensity values to form an image. As previously discussed, in PEDS pixels per se are not used to generate an image. However, due to the nature of currently available display devices (e.g., computer monitors), pixels are involved in displaying an image for viewing.

The two types of SNR, namely $signal_{spec}/noise_{bkg}$ and $signal_{spec}/noise_{spec}$, were measured. Fluorescently labeled polystyrene beads of 1.9 μm diameter were used to measure $signal_{spec}/noise_{bkg}$ values. These beads were selected because a large number of image frames could be collected without significant photo-bleaching. The second type of SNR, namely $signal_{spec}/noise_{spec}$, was measured using a uniformly fluorescent slide or a uniformly reflective tungsten-coated silicon substrate. Hibbs et al., Ch. 36 in Pawley (Ed.), *Handbook of Biological Confocal Microscopy*, $3^{rd}$ Ed., pp. 650-671, 2006. In both cases, photon-event files having an increasing number of detected photons were collected and imaged using both the PEDS and binning processes.

Figure 8:
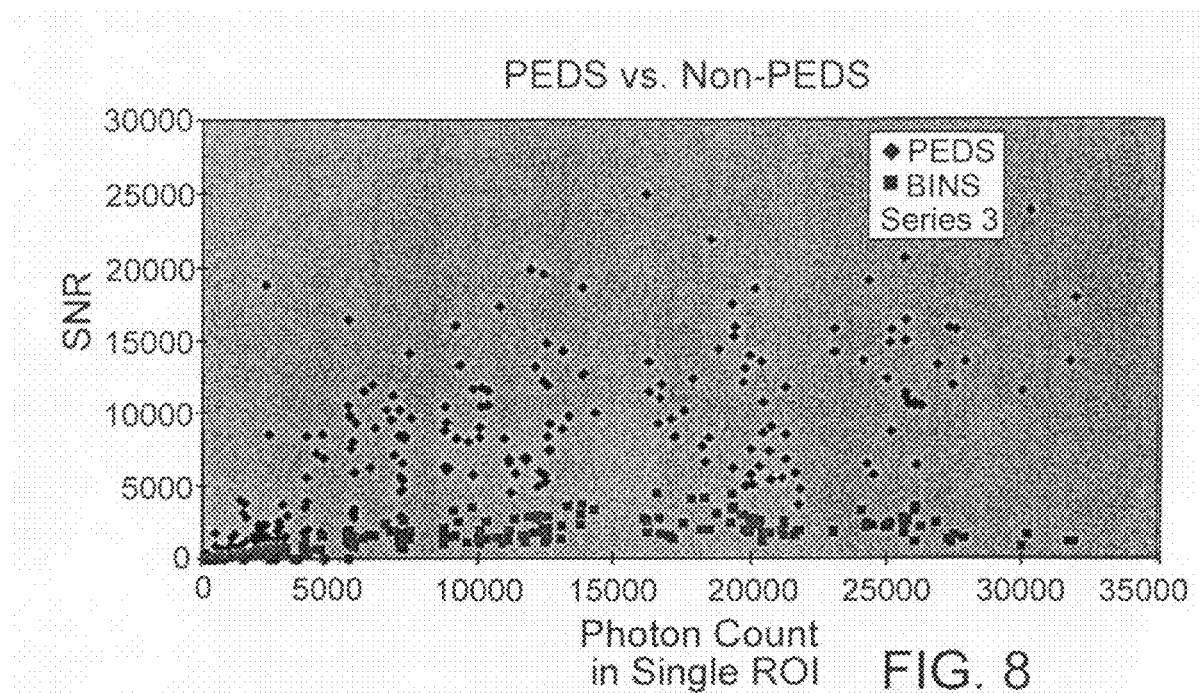
FIG. 8 is a scatter plot, discussed in Example 4, of signal-to-noise ratio ("SNR," which is the signal from the specimen ($signal_{spec}$) divided by the standard deviation of the signal obtained from a background region ($noise_{bkg}$)) values (denoted on the ordinate), as measured for images formed from the same image-data sets containing the registered locations of detected photons using either PEDS (dark diamonds) or conventional binning (lighter squares). Uniformly fluorescent, 1.9-μm diameter polystyrene beads were imaged using increasing excitation-light intensities to produce a range of photon counts (abscissa) in a region of interest (ROI) placed within the boundaries of the bead and used to collect the specimen signal values. Background noise values were obtained as the standard deviation of the mean photon-flux signal in a ROI of identical size placed sufficiently distant from the bead so that the recorded values were not influenced by photons coming from photons emitted by fluorophores in the bead.
Figure 9:
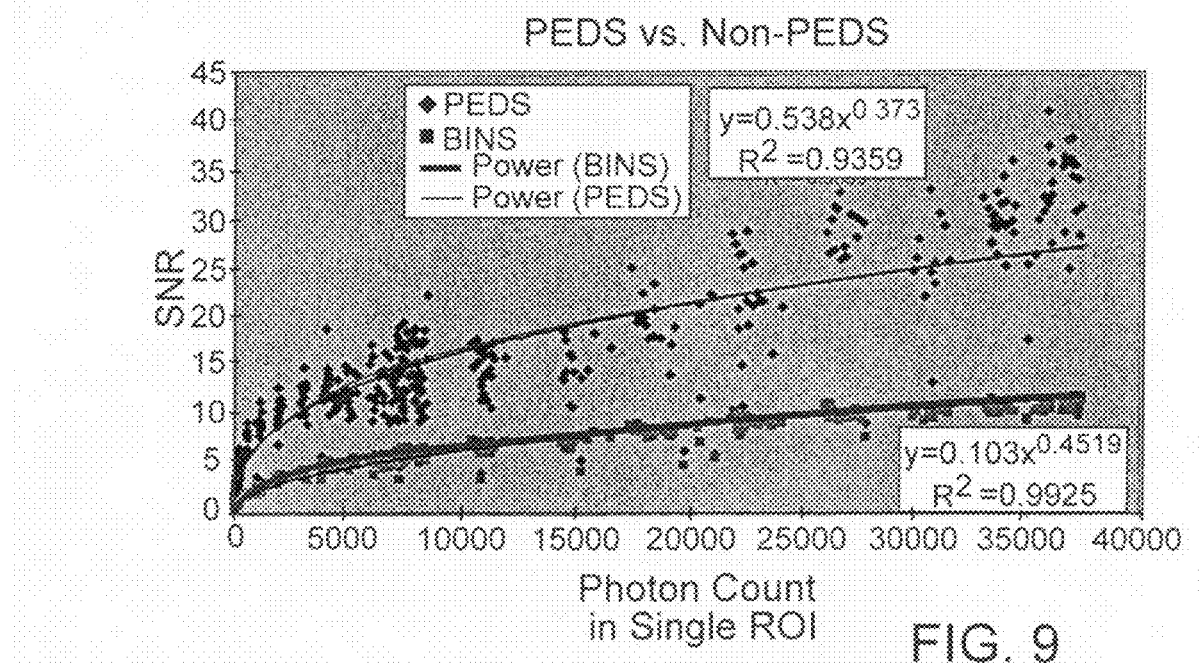
FIG. 9 is a scatter plot, obtained in Example 4, of SNR ($signal_{spec}$/$noise_{spec}$) values (ordinate) measured for images formed from the same photon-event files using either PEDS (dark diamonds) or conventional binning (lighter squares). A uniform reflective surface consisting of tungsten deposited on silicon was imaged using increasing excitation-light intensities to produce a range of photon counts (abscissa) in a region of interest (ROI) placed in the center of the image and used to define the area from which both the specimen signal and specimen signal noise (standard deviation of mean specimen signal values) values were measured. Individual values are indicated by the symbols, while the lines represent a power function fit to these values.

The results obtained are shown in FIGS. 8 and 9. FIG. 8 is a scatter plot of SNR ($signal_{spec}/noise_{bkg}$) values (ordinate) measured for images formed from the same photon-event files using either PEDS (dark diamonds) or conventional binning (lighter squares). Uniformly fluorescent, 1.9-μm diameter polystyrene beads were imaged using increasing excitation-light intensities to produce a wide range of photon counts (abscissa) in a region of interest (ROI) placed within the boundaries of the bead and used to collect the specimen signal values. Background noise values were obtained as the standard deviation of the mean photon-flux signal in a ROI of identical size placed sufficiently distant from the bead so that the recorded values were not influenced by photons coming from fluorophores in the bead. FIG. 9 is a scatter plot of SNR (signal$_{spec}$/noise$_{spec}$) values (ordinate) measured for images formed from the same photon-event files using either PEDS (dark diamonds) or conventional binning (lighter squares). A uniform reflective surface consisting of tungsten deposited on silicon was imaged using increasing excitation-light intensities to produce a wide range of photon counts (abscissa) in a region of interest (ROI) placed in the center of the image and used to define the area from which both the specimen signal and specimen signal noise (standard deviation of mean specimen signal values) values were measured. Individual values are indicated by the symbols, while the lines represent a power function fit to these values. Similar results were obtained when a uniformly fluorescent plastic slide was used as a specimen.

In each case, SNR values in PEDS images exceeded those in conventional binning images by factors of 4 to 6. Due to the nature of the relationships involved, large differences in the intensities of the illumination light produced similar SNR values using PEDS and binning under different imaging conditions.

Example 5

The results in Example 4 show that images can be formed more efficiently with PEDS, or alternatively that PEDS requires fewer photons to form an image comparable to that obtained with a greater number of photons with binning. In the current example, two studies were conducted to assess the practical significance of this. First, the extent to which 500-nm fluorescent polystyrene beads photo-bleached during a 30-minute period of continuous laser illumination when images were formed with either PEDS or binning process was assessed. This involved the use of a ±0.2 volt galvanometer signal range. In a second study, actin filaments in a fibroblast cell were imaged. These images required a greater scanned area and a galvanometer signal range of ±2.0 volts. In both cases, an illumination-light intensity typical of that employed in commercially available laser scanning confocal microscope systems was used to obtain SNR values typical of those obtained by binning. The excitation intensity of the laser was then adjusted to obtain a SNR value for PEDS that was similar or up to 2× greater than that resulting from binning.

Figure 10:
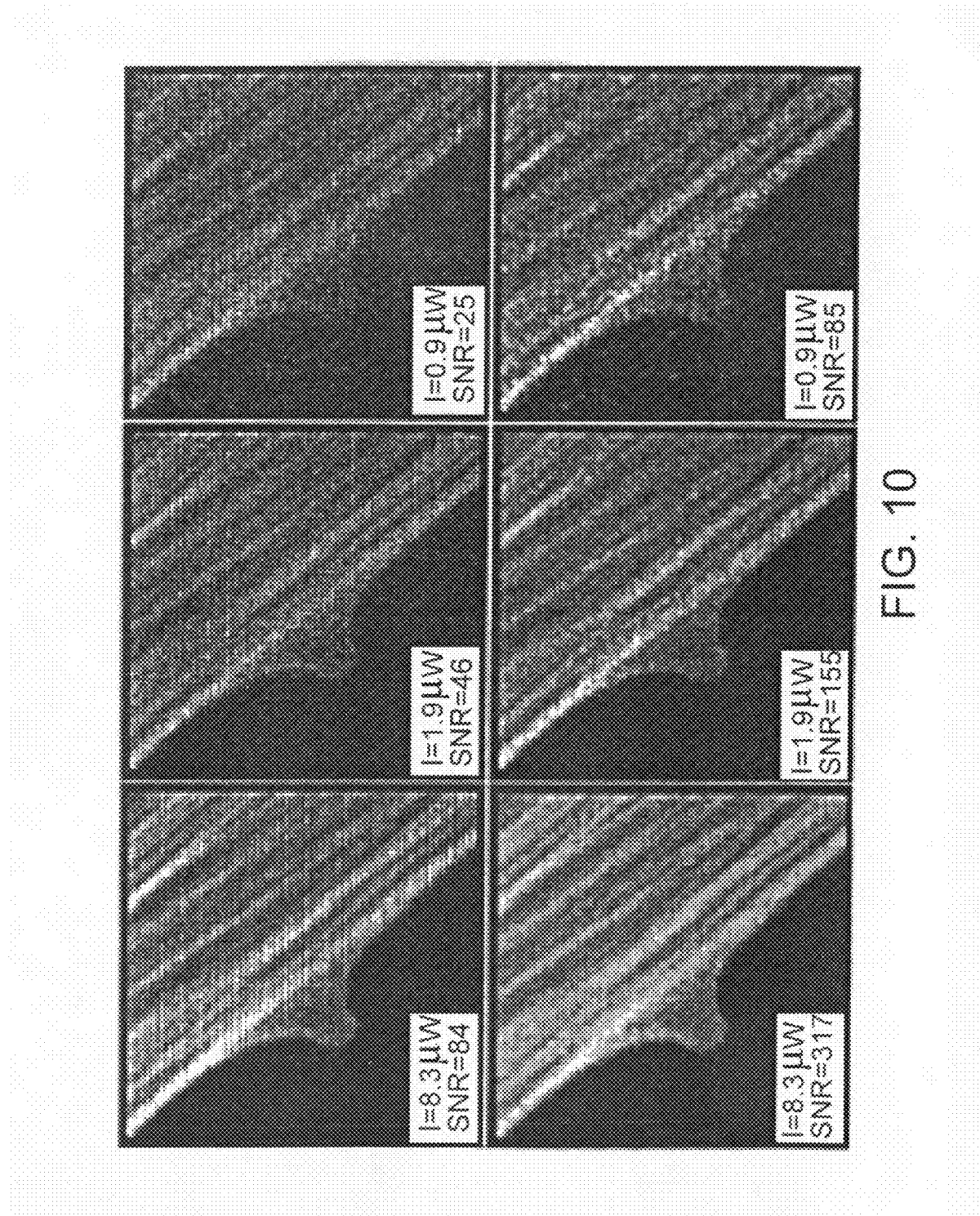
FIG. 10 depicts results, discussed in Example 5, of experiments in which actin filaments in chemically preserved cells were imaged. Photon-position data sets were obtained from the same specimen region using three different illumination-light intensities, and images from each data set were formed using PEDS (bottom row) or conventional binning (top row). SNR ($signal_{spec}$/$noise_{bkg}$) values and excitation-light intensities (I) are provided.

Results from the second test, which involved imaging actin filaments in chemically preserved cells, are shown in FIG. 10. In this study photon-event files were obtained from the same specimen region using three different illumination-light intensities. Images from the three photon-event files were then formed using either PEDS or binning. Although evaluation of the detail discernable in complex images such as these is subjective and dependent on the objective of the experiment, SNR, signal$_{spec}$/noise$_{bkg}$, values are provided. These images demonstrate that comparable image detail can be obtained with PEDS using 5-10 times lower excitation-light intensities than required with binning.

Specifically, FIG. 10 shows images of actin fibers stained with phalloidin labeled with Alexa-488 obtained from the same cell region. The photon-event files used to generate the images shown in images 1-3 in each row were obtained at laser illumination-light intensities (I) of 8.3, 1.9, and 0.9 microwatts. Images in the top and bottom rows were formed using binning and PEDS, respectively. The SNR (signal$_{spec}$/noise$_{bkg}$) values obtained for each image are shown in the bottom left corner of each image, as a quantitative measure of image quality. Illumination intensities were adjusted in each case from an initial level typical of that used routinely in a commercially available laser scanning confocal system to result in approximately a 2-fold reduction in the SNR associated with each series of images.

Technical limitations may also exist, wherein use of more efficient (e.g., 16-bit) ADCs and position-feedback signals having greater positional resolution likely increase PEDS efficiencies in these applications relative to binning as scanned areas are increased. The relationship between the size of the scanned region and the positional resolution of this PEDS example suggests that the magnification factor of the objective used has an impact on image-formation. For example, 100× and 60× objectives both having NA=1.45 should result in the same diffraction-limited spatial resolution in an image. However, the 100× objective should result in a greater positional resolution with PEDS and permit an image to be formed more efficiently than with the 60× objective.

The ability, using PEDS (as an example DEDS method), to form images from fewer detected photons has several consequences. First, images having SNR values comparable or superior to those obtained with binning can be obtained at the same scanning rates with PEDS using reduced excitation-light intensities. When fluorescent light is being imaged, photo-bleaching of fluorophores present in the specimen (living or preserved) and associated photo-toxicity in living specimens can be problematic and limit the number of images that can be obtained. Since photo-bleaching and photo-toxicity increase as the intensity of the illumination light is increased, the use of PEDS results in a decreased incidence of both events. Thus, specimens can be imaged for longer periods of time. Second, if necessary, the use of PEDS would also permit a greater number of image frames to be averaged to decrease image SNR values to even greater extents. Third, if similar excitation-light intensities are used, images with comparable SNR values can be obtained using faster scan rates with PEDS than with binning. Fourth, since fewer photons are required to form images having comparable SNR values using PEDS, the size of the pinhole aperture placed in front of the detector in a scanning confocal microscope system can be reduced to produce optical-image sections having less out-of-focus light in the z-axis than can be achieved using binning. Fifth, other than using a detector such as a photomultiplier or avalanche photodiode, in a photon-counting mode and the ability to trigger the acquisition of photon x, y position coordinates, no other complexities in the optical system are required with PEDS. Photon counting has long been recognized to be superior in performance to integrating detected photon events as analog signals.

In the embodiments described above, the scan format is a type of non-raster scan identified as a spiral scan. Other scan formats alternatively may be utilized, including other raster and non-raster scan formats.

As illustrated by the foregoing results, advantages of DEDS are increased SNR and all accompanying consequences, including (but not limited to): (a) fewer detected events are required to form images; (b) images can be obtained either more rapidly using a given intensity of excitation energy or with lower excitation-energy intensities with longer illumination intervals; (c) fluorescent images can be obtained of both live and preserved specimens, with less photo-bleaching and/or other photo-toxicity; and (d) images of live specimens can be obtained for longer periods of time with reduced levels of photo-toxicity. The ability to form images more efficiently is of particular importance in, for example, genetic-screening applications, such as micro-array analysis and chromosome labeling, where low numbers of fluorescent molecules are present and a reduced number of photons is available for detection.

It is to be understood that the foregoing is a description of preferred and other embodiments. The foregoing description therefore is not to be construed as itself limiting of the scope of the invention.

What is claimed is:

1. A method for producing a set of imagable data on discrete events associated with a specimen, comprising:
   detecting the discrete events occurring during an image-acquisition period;
   obtaining respective location data for the detected events, the location data corresponding to respective sites of origin of the detected events in or on the specimen;
   assigning to the location data, for each relevant detected event, a distribution determined by a probability-density function (PDF) to produce a set of imagable data.

2. The method of claim 1, wherein the discrete events are respective radiant events.

3. The method of claim 2, wherein each radiant event involves at least one respective photon.

4. The method of claim 2, wherein the radiant events involve at least one of transmission, reflection, fluorescence, and chemiluminescence.

5. The method of claim 1, further comprising:
   summing the imagable data; and
   displaying an image of the summed data.

6. The method of claim 1, further comprising:
   storing the imagable data in a memory;
   recalling the data from the memory; and
   processing the recalled data to form, from the data, an image of the discrete events.

7. The method of claim 6, wherein processing the data comprises:
   processing a first set of imagable data obtained in a first unit of sampling time;
   processing a second set of imagable data obtained in a second unit of sampling time;
   comparing the first and second sets of processed data; and
   displaying a result of the comparison.

8. The method of claim 1, further comprising exposing the specimen to a discrete-event stimulus to produce the discrete events on or in the specimen.

9. The method of claim 1, wherein the discrete-event stimulus is a laser beam.

10. The method of claim 1, wherein the location data comprise corresponding temporal data pertaining to respective times of the detected events from a beginning of the image-acquisition period.

11. The method of claim 1, wherein:
    the discrete events comprise respective photons propagating from the specimen; and
    the photons are detected using a photon detector.

12. The method of claim 1, wherein:
    obtaining the respective location data comprises scanning involving moving the specimen, in a scan pattern, relative to the detector; and
    monitoring specimen position in the scan pattern.

13. The method of claim 1, wherein:
    obtaining the respective location data comprises scanning involving moving the detector, in a scan pattern, relative to the specimen; and
    monitoring detector position in the scan pattern.

14. The method of claim 1, wherein:
    obtaining the respective location data comprises scanning involving moving an energy beam, in a scan pattern, relative to the specimen as the energy beam is incident to the specimen; and
    monitoring beam position in the scan pattern.

15. A method for producing an image of at least a region of interest of a specimen, comprising:
    detecting discrete events occurring on or in the region of interest;
    in an image-acquisition period and for each detected discrete event, obtaining corresponding location data;
    determining, from the location data, corresponding origin locations of the detected events;
    selecting a probability-density function (PDF);
    convolving each of the determined origin locations with the PDF;
    summing the PDF data over the image-acquisition period;
    processing the summed PDF data for display; and
    displaying the processed data as an image.

16. The method of claim 15, wherein the discrete events are respective photon events.

17. The method of claim 16, further comprising passing photons from photon events occurring on or in the specimen through a microscope optical system to a photon detector.

18. The method of claim 15, wherein the PDF is calculated or determined empirically, based on instrumentation used for performing the method, properties of the specimen, and nature of the discrete events.

19. A system for producing data pertaining to discrete events occurring on or in a region of interest of a specimen, comprising:
    a discrete-event detector that is positionable relative to the region of interest to detect discrete events occurring in the region of interest;
    a location-determining device associated with the detector and configured to determine respective locations of detected discrete events in the region of interest; and
    a computer connected to the detector and location-determining device, the computer being programmed to convolve the determined locations with a probability-density function (PDF) and to correlate the summed PDFs with the determined locations.

20. The system of claim 19, wherein:
    the computer is further configured to sum the PDFs in the image-acquisition period; and
    the system further comprises a display driver connected to the computer and a display connected to the display driver.

21. The system of claim 19, wherein:
    the discrete events comprise photons;
    the discrete-event detector comprises a photon detector; and
    the system further comprises an optical system situated between the photon detector and the region of interest.

22. A system for imaging a specimen, comprising:
    a radiant-event detector placed relative to the specimen:
    a scanner comprising a location-determining device;
    a scanner driver connected to the scanner to drive the scanner to any of multiple positions in a scan pattern in a region of interest of the specimen;
    a location sensor configured, for radiant events detected by the detector, to determine corresponding locations in the scan pattern;
    a computer connected to the detector, scanner driver, and location sensor, the computer being configured to convolve each detected location with a probability-density function (PDF) and to sum the PDFs; and a display connected to the computer to receive the summed PDFs from the computer.

23. The system of claim 22, further comprising a radiant-event stimulator, wherein the scanner is coupled to the radiant-event stimulator and configured to move the radiant-event stimulator over the scan pattern.

24. The system of claim 23, wherein the radiant-event stimulator is a laser beam.

25. A method for generating image data, comprising:

scanning a specimen during an image-acquisition period over a scan pattern comprising a plurality of scan positions;

detecting discrete events produced on or in the specimen during the image-acquisition period;

detecting respective locations associated with the discrete events in the scan pattern;

selecting at least one probability-density function (PDF);

applying the at least one PDF to the detected locations;

summing the applied PDFs to obtain at least one PDF distribution; and converting the at least one PDF distribution to image data.

* * * * *